United States Patent [19]

Floyd, Jr. et al.

[11] 4,250,325
[45] Feb. 10, 1981

[54] NOVEL 15-DEOXY-16-ETHYNYL AND -16-(1-PROPYNYL)-1-CARBOXY AND 1-CARBINOL PROSTAGLANDINS OF THE A, D, E AND F SERIES

[75] Inventors: Middleton B. Floyd, Jr., Suffern, N.Y.; Martin J. Weiss, Oradell, N.J.; Charles V. Grudzinskas, Nyack, N.Y.; Sow-Mei L. Chen, Park Ridge, N.J.

[73] Assignee: American Cyanamid Company, Stamford, Conn.

[21] Appl. No.: 969,479

[22] Filed: Dec. 14, 1978

Related U.S. Application Data

[63] Continuation-in-part of Ser. No. 857,848, Dec. 5, 1977, Pat. No. 4,190,596, Ser. No. 857,849, Dec. 5, 1977, Pat. No. 4,190,597, and Ser. No. 857,714, Dec. 5, 1977, Pat. No. 4,191,699, each is a continuation-in-part of Ser. No. 706,343, Jul. 19, 1976, Pat. No. 4,061,670.

[51] Int. Cl.³ .......................................... C07C 177/00
[52] U.S. Cl. ..................................... 560/121; 562/503
[58] Field of Search ........................ 560/121; 562/503

[56] References Cited

U.S. PATENT DOCUMENTS 4,132,738   1/1979   Kluender ........................... 260/586

Primary Examiner—Robert Gerstl
Attorney, Agent, or Firm—Richard J. Hammond

[57] ABSTRACT

The invention described herein relates to novel 15-deoxy-16-hydroxy-16-ethynyl or 16-(1-propynyl) prostaglandins of E, F, D and A series having on the terminal methylene carbon of the alpha chain a substituent selected from the group consisting of:

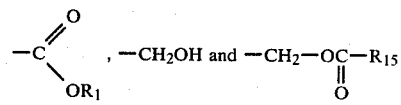

wherein $R_1$ is selected from the group consisting of hydrogen and $C_1-C_6$ alkyl; $R_{15}$ is selected from the group consisting of $C_1-C_4$ alkyl, di-$C_1-C_4$-alkylamino, phenyl and phenyl substituted with one or more substituents selected from the group consisting of $C_1-C_4$ alkyl, OR, SR, F or Cl, wherein R is an alkyl group.

8 Claims, No Drawings

NOVEL 15-DEOXY-16-ETHYNYL AND -16-(1-PROPYNYL)-1-CARBOXY AND 1-CARBINOL PROSTAGLANDINS OF THE A, D, E AND F SERIES

This application is a continuation-in-part of the following currently pending applications: Ser. Nos. 857,848, now U.S. Pat. No. 4,190,596 857,849, now U.S. Pat. No. 4,190,597 and 857,714, now U.S. Pat. No. 4,191,699 all filed on Dec. 5, 1977; said applications are continuations-in-part of the parent application, Ser. No. 706,343, filed July 19, 1976 now U.S. Pat. No. 4,061,670.

BACKGROUND OF THE INVENTION (1) Field of the Invention

The present invention relates to 15-deoxy-16-hydroxy-16-ethynyl and 16-substituted ethynyl prostaglandins, as well as the pharmaceutically acceptable, non-toxic lower alkyl esters and salts thereof, and to the intermediates and processes for producing such compounds.

(2) Background of the Invention

Prostaglandins have classically been described as chemically related 20 carbon chain hydroxy fatty acids having the basic skeleton of prostanoic acid:

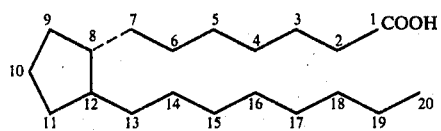

The prostaglandins having a hydroxyl group at the C-11 position and a keto group at the C-9 position are known as the PGE series, and those having a hydroxyl group in place of the keto group are known as the PGF series and are further designated by an or suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, S. Bergström, *Recent Progress in Hormone Research* 22, pp. 153–175 (1966) and *Science* 157, page 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axes et al, *Synthesis* Vol. 1, John Wiley and Sons Inc., New York, N. Y. 1973 and P. H. Bently, *Chem. Soc. Reviews* 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Patent No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared [see for example, U.S. Pat. No. 3,950,406; *Prostaglandins*, Vol. 10, 733 (1975); *Tetrahedron Letters*, No. 48, 4217 (1975)].

Recently reports have also appeared wherein the C-16 carbon bearing a hydroxyl group is substituted with a methyl group [see Pappo et al, *Tetrahedron Letters*, No. 4, 235 (1975); Collin et al, U.S. Pat. No. 3,965,143; and Belgium Patent No. 827,127].

Recently the synthesis of some PGE, controls has been reported. The carbinol compounds synthesized therein were reported to exhibit more specific activities than natural PGt., Kluender et al., *Tetrahedron Letters* No. 24, 99. 2063–2066 (1977).

The 15-deoxy-16-hydroxy-16-vinyl and 16-cyclopropyl analogs of the E, F, A, and D series have been described in U.S. Pat. No. 4,061,670, the grandparent of this application.

SUMMARY OF THE INVENTION

In accordance with the present invention, we have prepared certain novel 15-deoxy-16-hydroxy-16-(1-propynyl), 15-deoxy-16-hydroxy-16-ethynyl and 16-substituted ethynyl-prostaglandin analogs represented by the following formula:

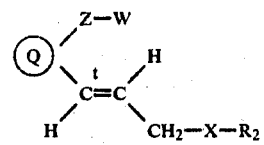

wherein Q is a divalent cyclopentyl moiety selected from the group consisting of:

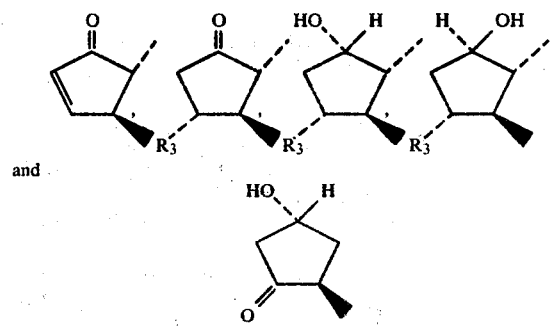

$R_3$ is selected from the group consisting of hydroxy and hydrogen; W is selected from the group consisting of

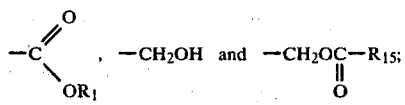

$R_1$ is selected from the group consisting of hydrogen, $C_1$–$C_6$ alkyl and various ester and amide groups as disclosed by Examples 24–188; $R_{15}$ is selected from the group consisting of $C_1$–$C_4$ alkyl; di-$C_1$-$C_4$-alkylamino, phenyl and phenyl substituted with one or more substituents selected from the group consisting of $C_1$–$C_4$ alkyl, OR, SR, F or Cl, wherein R is $C_1$-$C_4$ alkyl; $R_2$ is selected from the group consisting of $C_3$-$C_7$ alkyl; X is selected from the group consisting of a divalent moiety of the formulae:

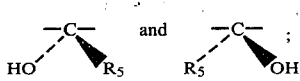

$R_5$ is selected from the group consisting of 1-propynyl, ethynyl and trimethylsilylethynyl; Z is selected from the group consisting of a divalent moiety of the formulae:

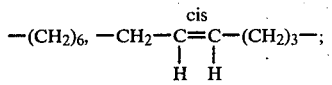

—$(CH_2)_4$—S—$CH_2$—, and —$(CH_2)_4$—O—$CH_2$—; with the proviso that when W is —$CH_2OH$, then Z cannot be —$(CH_2)_4$—S—$CH_2$ or —$(CH_2)_4$—O—$CH_2$), Q cannot be

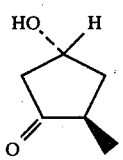

and $R_3$ must be hydroxy; the racemic mixture thereof; the mirror image thereof; and when $R_1$ is hydrogen, the pharmacological acceptable salts thereof.

The dotted lines shown in the above formula and in the formulas below indicate that the substituents are in α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual 8R enantiomers are encompassed within the scope of the present invention.

When the compounds of the present invention are racemic mixtures, they are produced starting from racemates; while when the compounds of the invention are individual enantiomers, the compounds are preferably obtained starting from the appropriate individual enantiomers.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g. lithium, sodium and potassium, and from the alkaline earth metals, e.g. magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and arylaliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N--(p-tertamylphenyl)diethanolamine, galactamine, N-methylglucamine, N-methylglucosamine, ephedrine, phenylephrine, epinephrine, procaine, and the like.

Examples of suitable pharmaclogically acceptable quaternary ammonium cations are tetramethylammonium, tetraethylammonium, benzyltrimethylammonium, phenyltriethylammonium and the like.

DETAILED DESCRIPTION OF THE INVENTION

The novel compounds of this invention can be prepared by a 1,4-conjugate-addition procedure involving treatment of the ether blocked cyclopentenone (18) with a lithiocuprate reagent such as (8) or (14) prepared as illustrated in Flowsheets A, B, C, D, E, F, G and H.

In accordance with the procedure outlined in Flowsheet A, treatment of bistrimethylsilylacetylene (1) with an acid chloride (2) in the presence of aluminum trichloride provides the acylacetylene (3). Treatment of the acylacetylene (3) with propargylic magnesium halide (4) forms the diacetylenic alcohol (5) which is silylated with chlorotrimethylsilane to provide the silyl ether (6). The silyl ether (6) is converted to the vinylstannane (7) by treatment with tributylstannane in the presence of azobisisobutrylnitrile.

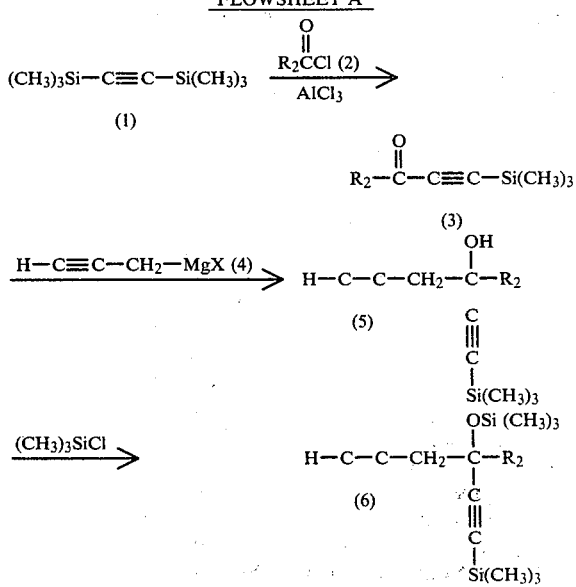

FLOWSHEET A

-continued
FLOWSHEET A

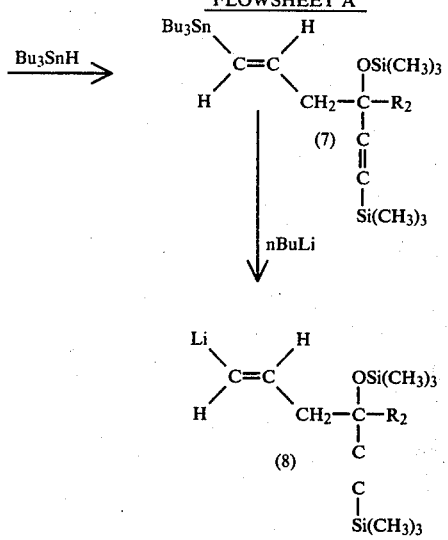

Treatment of the vinylstannyl reagent (7) with n-butyl lithium at a temperature of −10° C. to −78° C. generates the vinyl lithium reagent (8).

In accordance with the procedure as outlined in Flowsheet B, an aldehyde (9) is treated with proparglic magnesium halide (4) to form the homopropargylic alcohol (10), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give the 1-iodo-4-trimethylsilyloxy-trans-1-alkene (11).

The trimethylsilyl protecting group is removed with mild acid and the resulting vinyl iodide alcohol is oxidized with pyridinium chlorochromate to provide the 1-iodo-4-oxo-trans-1-alkene (12) which upon treatment with a Grignard reagent ($R_5MgX$) or alkyl lithium ($R_5Li$) provides the 1-iodo-4-hydroxy-trans-1-alkene, which is silylated in the usual manner to provide the silyl ether (13).

Treatment of (13) at low temperature, preferably −30° C. to −78° C. in an inert solvent, e.g., hexane, ether or toluene, with an alkyl lithium, e.g. n-butyl lithium or t-butyl lithium (2 equivalents) provides the trans-1-alkenyl lithium reagent (14). In the case of the vinylstannyl (7), n-butyl lithium is preferred for the generation of the vinyl lithium reagent.

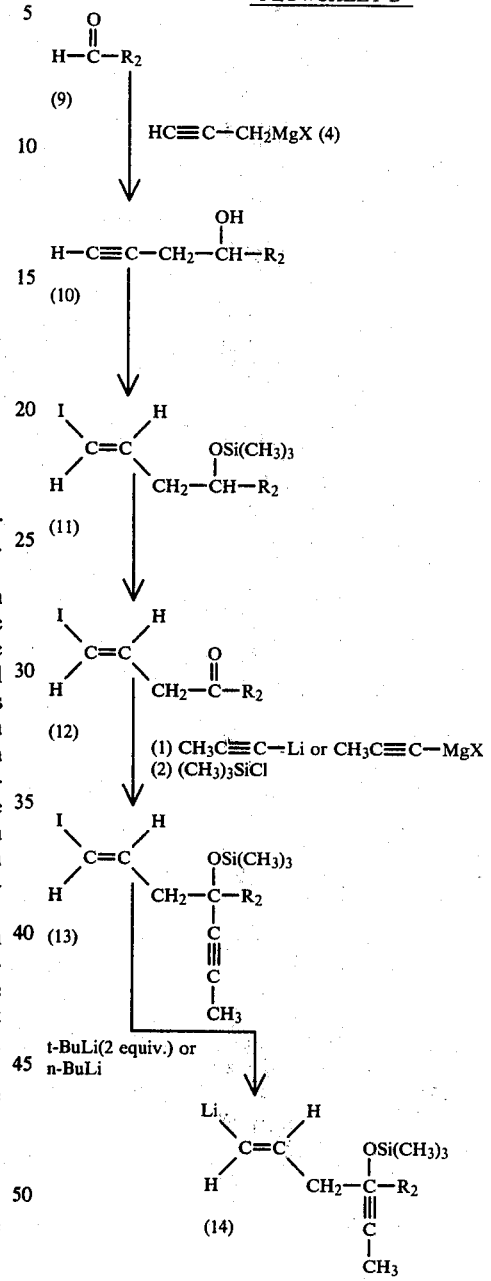

FLOWSHEET B

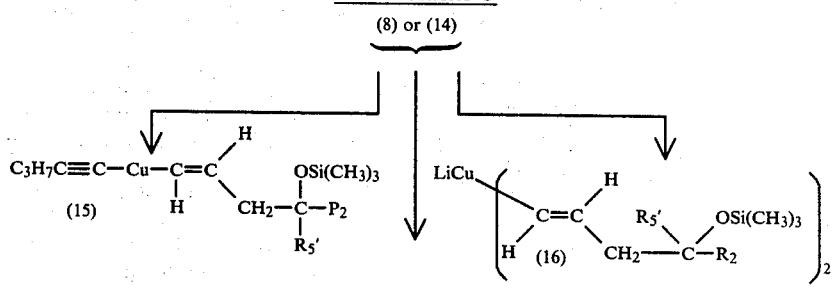

FLOWCHART C

FLOWCHART C

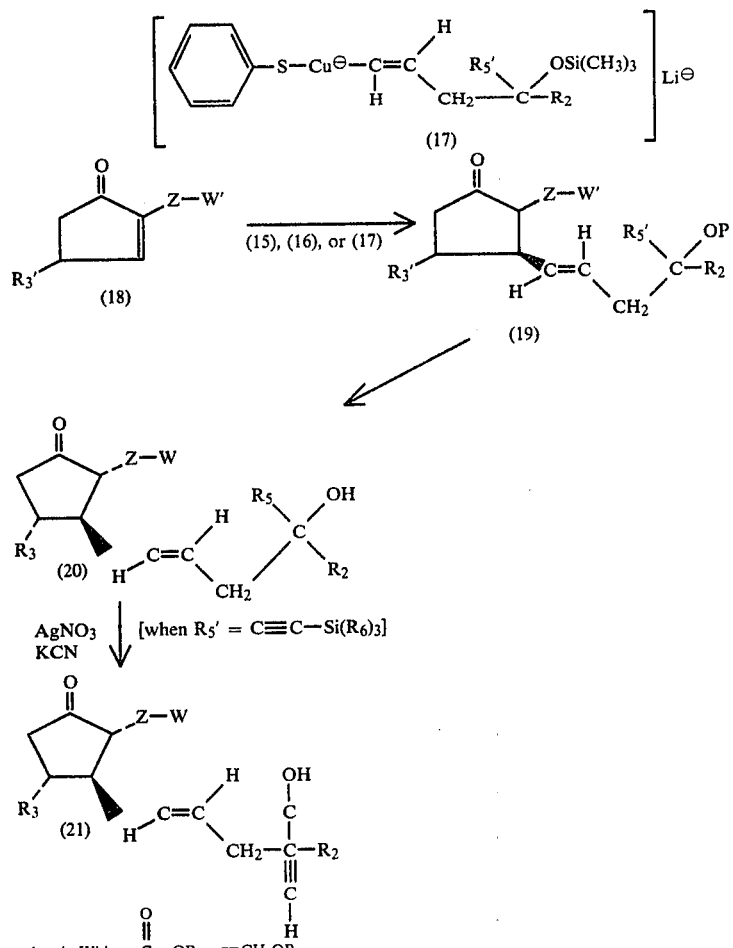

wherein W' is —C—OP or —CH₂OP;
wherein P is a protecting group such as 1-methoxy-1-methyl-ethyl, 1-methoxy ethyl, 1-methyl-1-ethoxy-ethyl, 1-ethoxyethyl, tetrahydropyranyl, tri($C_1$—$C_4$)-alkylsilyl, or ($C_1$—$C_6$) alkyl;
$R_3'$ is hydrogen or —OP;
wherein P is defined as above; $R_3$ is hydrogen or hydroxy; $R_5'$ is 1-propynyl or tri($C_1$—$C_4$) alkylsilylethynyl;
$R_6$ is ($C_1$—$C_4$) alkyl.

In accordance with Flowsheet C, for the preparation of the asymmetrical lithio cuprate (15), wherein $R'_5$ is —C≡C—CH₃ or —C≡C—Si($R_6$)₃, or the like, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about −78° C. After about one hour at this temperature, a molar equivalent of the requisite cyclopentenone (18) is added. After several hours at −30° C. to −70° C. the reaction mixture is quenched with aqueous ammonium chloride solution and the blocked product (19) is isolated in the usual manner.

It is also possible to effect conjugate 1,4-addition with the asymmetrical lithio cuprate (17) wherein $R'_5$ is —C≡C—CH₃ or —C≡C—Si($R_6$)₃ derived from vinyl lithium and cuprous thiophenoxide. A solution of vinyl (8) or (14) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio cuprate (17) is treated with the requisite cyclopentenone (18) as described hereinabove for the conjugate addition with 1-alkynyl lithio cuprate (16).

For the preparation of symmetrical lithio cuprate (16) wherein $R'_5$ is —C≡C—CH₃ or —C≡C—Si($R_6$)₃ one molar equivalent of copper (I) iodide tributylphosphine complex, dissolved in anhydrous ether, is added at about −78° C. to two molar equivalents of the aforementioned vinyl lithium (8) or (14) solution cooled to −78° C. After about one hour at this temperature, the lithio cuprate (16) is treated with the requisite cyclopentenone (18) as described hereinabove for the conjugate addition with the 1-alkynyl lithio cuprate (15).

The procedures for conjugate addition involving organocopper reagents are well known in the art, see for example C. J. Sih, et al, *J. Amer. Chem. Soc.*, 97, 865 (1975). Many esters and amide functions, such as those described in Examples 24 to 188 may be used as protecting groups in place of P during the conjugate addition.

In the cases where P=trimethylsilyloxy in cyclopentenone (18) the conjugate addition is performed at −78° C. to −40° C. The reaction is quenched by addition of an either solution of acetic acid. Removal of blocking groups is then carried out as described in the reference above to provide the product (20) wherein $R_1,R_2$ are as hereinabove defined and $R_3$ is hydrogen or hydroxyl.

To prepare the prostaglandin wherein the $R_5$ group at C-16 is —C≡CH, the precursor (20) wherein $R'_5$ is —C≡C—Si$(R_6)_3$ is treated with aqueous silver nitrate followed by potassium cyanide to cleave the silylcarbon bond. An alternate procedure involves the use of silver salts such as AgBF$_4$. An additional procedure which may be used to cleave the silylcarbon bond involves treatment with potassium fluoride in dimethylformamide.

The introduction of a racemic β-chain possessing the 16-hydroxy-16-ethynyl moieties provides a pair of prostaglandins epimeric at C-16. These two epimers may be separated into their upper (less polar) and lower (more polar) componnents by high-pressure liquid chromatography (HPLC) or by dry-column or preparative thin layer silica-gel chromatography.

All available evidence leads up to believe that the —CH≡CH— function introduced by the cuprate process occupies a position trans to the 11-oxy function. Similarly, we are led to the conclusion that in the product (19) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ε. In order to ensure a trans-relationship in (19) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triloweralkylsilyloxy substituted lithio cuprate reagents of type (8) and (14) and their iodo and trialkylstannyl precursors are novel and useful compounds which are also embraced by this invention. They may be defined by generic formulae (B) and (C).

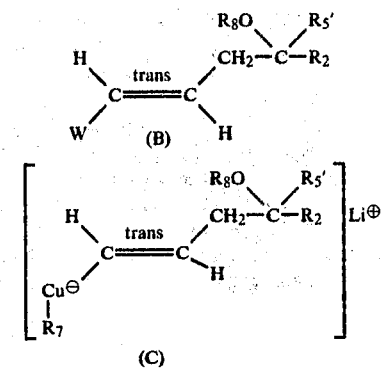

wherein W is iodine, tri n-butylstannyl or lithium, $R_2$ and $R'_5$ are as hereinabove defined, $R_8$ is triloweralkylsilyl, $R_7$ is thiopheneoxide, substituted thiopheneoxide, and alkyne or the identical vinyl moiety.

The cyclopentenones required for the preparation of the $E_1$, $E_2$, 3-oxa, and 11-deoxy-3-thia series as well as the $E_1$-1-carbinol series* have been described in the literature. The cyclopentenone for the preparation of 3-thia-11-hydroxy prostaglandins is described in Flowsheet D. The cyclopenenone for the $E_2$-1-carbinol series is described in Flowsheet E.

*Miles, Tetrahedron Letters, 2063–66(1977)

In accordance with Flowsheet D which is hereinbelow described, treatment of 2-furyl lithium (22A) with a ω-chloroaldehyde (22B) provides the chloroalcohol (22C). Treatment of the chloroalcohol (22C) with ethylmercaptoacetate furnishes the hydroxyester (22D) which upon hydrolysis with sodium formate/formic acid provides the 3-hydroxy-cyclopentenone (22E). Treatment of the cyclopentenone (22E) with sulfuric acid provides the required 4-hydroxy-cyclopentenone (22F) which after treatment with chlorotrimethylsilane provides the bissilylated cyclopentenone (22G).

FLOWSHEET D

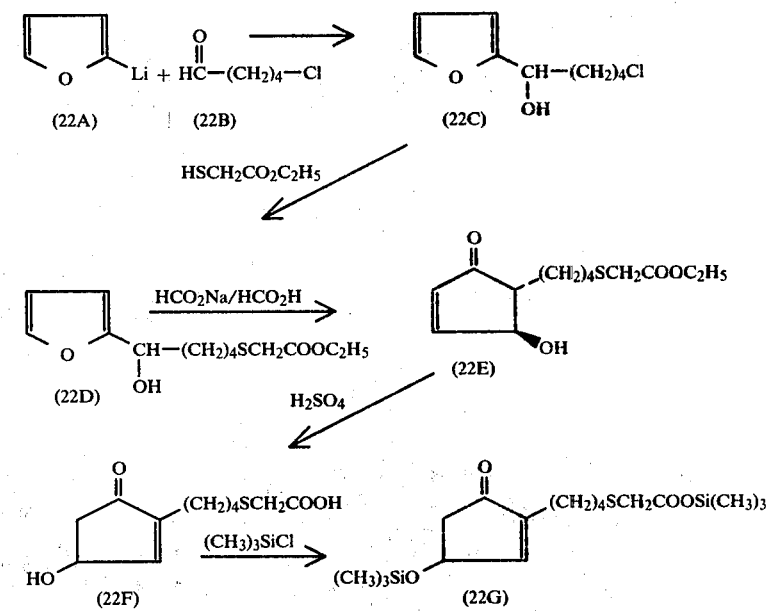

In accordance with Flowsheet E which is hereinbelow described, a solution of 2,5-dihydro-2,5,dimethoxy-2-(7-carboxy-3-cis-heptenyl)furan (22H) in toluene is added to a solution of sodium bis-(2-methoxyethoxy) aluminum hydride in toluene at 75° C., causing reduction of the 7' carboxyl of the furan and yielding the 2,5-dihydro-2,5-dimethoxy-2-(8'-hydroxy-3'-cis-octenyl) furan (22I). The 8' hydroxy furan (22I) is made to rearrange to form the 2-(7'-hydroxy-2'-cis-heptenyl)-4-hydroxy cyclopent-2-cis-1-one (22J) by treatment of a buffered solution of the 8' hydroxy furan (22I) with hydroquinone, refluxing the resulting mixture for about 24 hours, cooling the mixture, acidifying the mixture, followed by refluxing the mixture for about 18 hours.

Treatment of the 4-hydroxy-cyclopentenone (22J) with 2-methoxypropane and dichloroacetic acid yields the bis-(2-methoxy-2-propyl) ether of the cyclopentenone (22K).

FLOWSHEET E

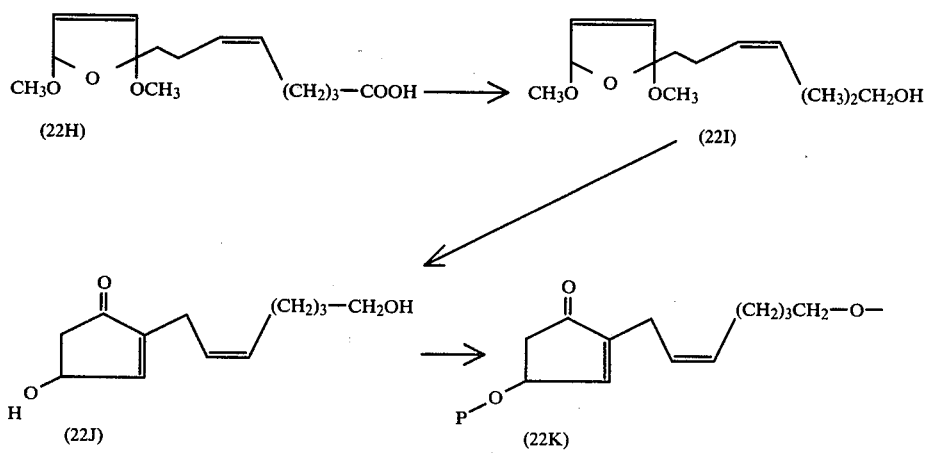

In accordance with Flowsheet F, when the 11-hydroxy or 11-oxy derivatives are treated with dilute acid, it is possible to effect elimination and the formation of the corresonding $\Delta^{10}$ derivatives (22M) of the prostaglandin A-type. A preferred procedure involves treatment in tetrahydrofuran: water (2:1) solvent 0.5 N in HCl for about 30 hours at ambient temperature.

Under these conditions a tetrahydropyranyl or trialkylsilyl ester or ether will undergo hydrolysis.

FLOWSHEET F

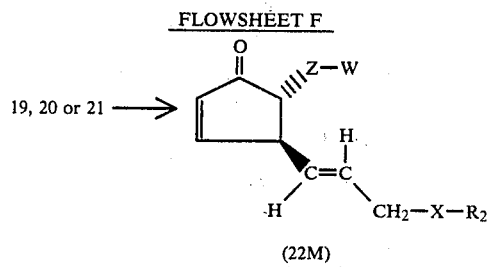

19, 20 or 21 →

FLOWSHEET G

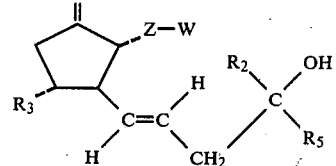

(23)

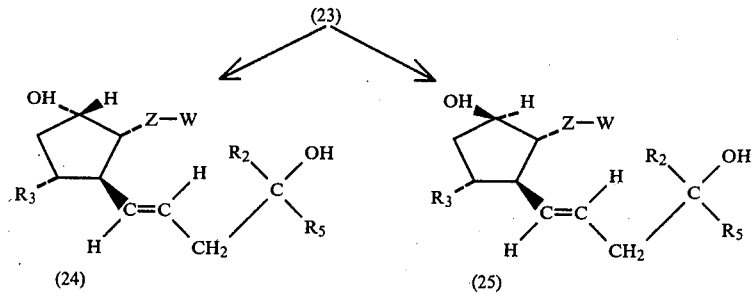

(24)                    (25)

As is illustrated by flowsheet G, when (23) is treated with lithium perhydro-9b-boraphenalyl hydride [See, H. C. Brown and W. C. Dickerson, J.A.C.S. 92, 709 (1970)] or lithium tris-(sec-butyl) borohydride [H. C. Brown and S. Krishnamurthy J.A.C.S. 94, 7159 (1972)], the product is at least predominantly the 9α-hydroxy derivative wherein the 9α-hydroxy group is cis to the side chain attached to $C_8$ and the the 11-oxy function, if present.

FLOWSHEET H

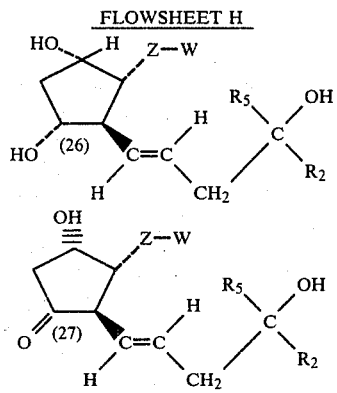

In accordance with flowsheet H, treatment of the PGF₂ analogs (26) with an oxidizing agent such as Jones reagent or pyridinium chlorochromate provides a selective oxidation of the 11α-hydroxyl group to provide the compounds of the PGD structure such as (27).

In accordance with the process of Bundy et al. J.A.C.S. 94, 2123 (1972) or E. J. Corey J.O.C. 38, 3187 (1973) which are incorporated by reference, the PGA₁ or PGA₂ type compounds of this invention, may be converted to the corresponding PGE₁ or PGE₂ series compound.

This conversion is accomplished by treating either the protected or unprotected PGA series compound of the formula:

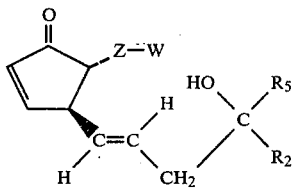

with alkaline hydrogen peroxide to provide a mixture of 10,11-epoxides which, without separation is reduced with chromous acetate in acidic acid or by aluminum amalgum to provide after hydrolysis (if necessary) and silica gel chromatography the 11-hydroxy PGE compounds and a lesser amount of the corresponding 11β-epimer.

The prostaglandin carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, *Organic Reactions*, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized product. [For a pertinent literature analogy see *Prostaglandins*, 4, 768 (1973).]

An alternative procedure involves treatment of the prostaglandin acid with a molar equivalent of the trialkylamine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. No. 2,365,205; *Chem. Abst.*, 81, 12009Bg (1974).

The amide derivatives of the prostanoic acids of this invention are also prepared in the usual manner by procedures well known in the art such as treatment with the appropriate isocyanate, substituted amine, hydrazine or other appropriate reagent.

The esterified alcohol drivatives of the carbinol compounds of this invention are also prepared in the usual manner by procedures well known in the art from the appropriate alkanoic or aryl acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information concerning high speed liquid chromatography and the instruments necessary for its application, is available from Waters Associate Inc., Maple Street, Milford, Mass.]

The hydroxycyclopentenone racemates may be resolved into their component enantiomers (28) and (29) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpenanoic acid hydrochloride (to give 30), (R)-2-aminoxy-3,3-dimethylbutyric acid hydrochloroide, and 4-methylbenzyl semicarbazide. After separation of the diastereomeric derivatives, reconstitution of the keto function provides the individual 4-hydroxycyclopentenone enantiomers (28) and (29). A useful procedure for the resolution of a 4-hydroxycyclopentenone racemate via an oxime such as (30) is described in the art [R. Pappo, P. Collins and C. Jung, *Tetrahedron Letters*, 943 (1973)]. The resolution of the hydroxycyclopentenone (28) wherein Z is

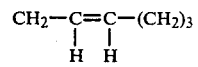

and R₃ is as previously defined is described by Bruhn et al., *Tetrahedron Letters*, 235 (1976).

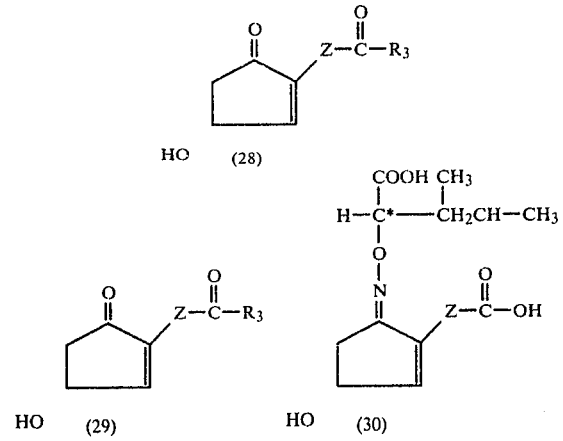

The ring system of certain of the novel compounds of this invention allow them to be characterized as follows:

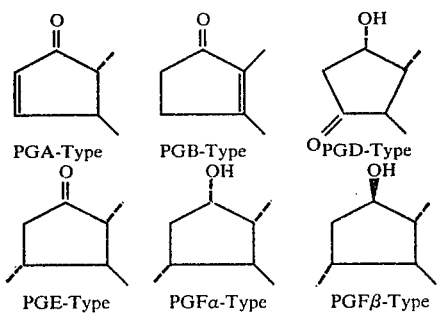

The known PGE, PGF$_\alpha$, PGF$_\beta$, PGA and PGD compounds are all potent in causing multiple biological responses even at low doses. For example, PGE$_1$ and PGE$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively, orally, sublingually, intravaginally, buccally, or rectally, in addition to the usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 11-deoxy-PGE, PGF$_\alpha$ and PGF$_\beta$ compounds are additionally selective in that they are at most relatively very weak stimulants of smooth muscle. The 11-deoxy PGE compounds have a further advantage in that they are much more stable and have a longer "shelf-life" than the corresponding 11-hydroxy derivatives as described more fully hereinbelow.

PGE$_1$, PGE$_2$, PGE$_3$ and dihydro-PGE$_1$, and the corresponding PGF$_\alpha$, PGF$_\beta$, and PGA, compounds, and their esters and pharmacologically acceptable salts, are extremely potent in causing various biological responses. For that reason, these compounds are useful for pharmacological purposes. See, for example, Bergstrom, et al., Pharmacol. Rev., 20, 1 (1968), and references cited therein. A few of these biological responses are systemic arterial blood pressure lowering in the case of the PGE, PGF$_\beta$, and PGA compounds as measured, for example, in anesthetized (phenobarbital sodium) pentolinium-treated rats with indwelling aortic and right heart cannulas; pressor activity, similarly measured, for the PGF$_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 ug to about 10 mg per ml of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 g to about 500 ug per kg of body weight per minute, or in a total daily dose by injection or infusion in the range of about 0.1 mg to about 20 mg per kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like to minimize their well-known ulcerogenic effects.

The PGE and PGD compounds are useful whenever it is desired to inhibit platelet aggregation, to reduce the adhesive character of platelets, and to remove or prevent the formation of thrombi in mannals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 mg to about 20 mg per kg of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g. oxytocin, and the various ergot alkaloids including derivatives and analogs thereof. Therefore $PGE_2$, for example, is useful in place of or in combination with less than usual amounts of these known smooth muscle stimulators, for example to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 ug to about 50 ug per kg of body weight per minute until the desired effect is obtained. Subsequent doses are given by intravenous, subcutaneous, or intramuscular injection or infusion during puerperium in the range of 0.01 mg to 2 mg per kg of body weight per day, the exact dose depending on the age, weight, and condition of the patient.

The PGE, $PGF_\beta$ and PGA compounds are useful as hypotensive agents to reduce blood pressure in mammals including man. For this purpose, the compounds are administered by intravenous infusion at the rate of about 0.01 ug to about 50 ug per kg of body weight per minute, or in a single or multiple doses of about 25 ug to 2500 ug per kg of body weight total per day.

The PGE, $PGF_\alpha$, and $PGF_\beta$ compounds are useful in place of oxytocin to induce labor in pregnant female animals, including man, cows, sheep, pigs, at or near term or in pregnant animals with intrauterine death of the fetus from about 20 weeks to term. For this purpose, the compound is infused intravenously at a dose 0.01 ug to 50 ug per kg of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started.

The PGE, $PGF_\alpha$, and $PGF_\beta$ compounds are useful for controlling the reproductive cycle in ovulating female mammals including humans and other animals. For that purpose, $PGF_2\alpha$, for example, is administered systemically at a dose level in the range of 0.01 mg to about 20 mg per kg of body weight, advantageously during a span of time starting approximately at a time of ovulation and ending approximately at the time of menses or just prior to menses. Additionally, expulsion of an embryo or fetus is accomplished by similar administration of the compound during the first third or the second third of the normal mammalian gestation period. Accordingly, they are useful as abortifacients. They are also useful for induction of menses during approximately the first two weeks of a missed menstrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrome and early kidney transplant rejection. In case of excessive or inappropriate ADH antidiuretic hormone vasopressin secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 2 to 2000 ug/ml of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluoroprednisoline, each of those being used in combination at the usual concentrations suitable for its use alone.

Furthermore, some $PGE_1$ carbinols have been shown to act as specific gastric antisecretory agents comparable to PGE with only low or undetectable side activities. Moreover, the carbinol derivatives were found not to effect smooth muscle at doses at lease 200 times those at which $PGE_1$ causes significant effects.

The novel compounds of this invention induce the biological responses described hereinabove as associated with its particular prostaglandin type. These novel compounds are accordingly used for the above-described corresponding purposes.

The novel PGE, $PGF_\beta$ and PGA compounds of this invention are also useful as bronchodiltors for the treatment of asthma and chronic bronchitis.

TABLE A

| | Bronchodilator Activity (Konzett Assays) | | | |
|---|---|---|---|---|
| | $ED_{50}$, mg./kg. Spasmogenic Agent | | | |
| Compound | 5-hydroxythryptamine | histamine | Acetyl-choline | potency* |
| dl-11α,16-dihydroxy-9-oxo-16-ethynyl-13-trans-prostenoic acid | 767× $10^{-6}$ | 968× $10^{-6}$ | 1.3 × $10^{-3}$ | 5 |
| methyl-11α,16-dihydroxy-9-oxo-16-ethynyl-13-trans-prostenoate | 16 × $10^{-3}$ | 1.4 × $10^{-3}$ | 2.4 × $10^{-3}$ | 4 |
| methyl-11α,16-dihydroxy-9-oxo-16-ethynyl-13-trans-prostenoate (more polar isomer) | | | | 2 |
| methyl-11α,16-dihydroxy-9-oxo-16-ethynyl-13-trans-prostenoate (less polar isomer) | | | | 5 |
| dl-11α,16-dihydroxy-9-oxo-16-ethynyl-5-cis-13-trans-prostadienoic acid | 571 × $10^{-6}$ | 389 × $10^{-6}$ | 987 × $10^{-6}$ | 5 |

*Potency is rated on a 0-5 scale, with 5 being the most potent.

As such they may be conveniently administered by inhalation of aerosol sprays prepared in a dose range of about 10 ug to about 10 mg/ml of a pharmacologically suitable liquid vehicle. Relative to the natural prostaglandins, the PGE compounds in particular have the significant advantage of inducing prolonged effects.

The invention will be described in greater detail in conjunction with the following specific examples.

EXAMPLE 1 n-Butyl trimethylsilylethynyl ketone

To a stirred solution of 14.4 grams of valeryl chloride and 20.4 grams of bis-trimethylsilylacetylene in 300 ml of dry methylene chloride, cooled in an ice bath, is added powdered anhydrous aluminum chloride, portionwise, over a period of 20 minutes. The mixture is stirred for 5 minutes, then the cooling bath is removed and the mixture stirred at room temperature for 4 hours. The mixture is poured into 500 ml of ice-water. The organic layer is separated, washed with water and brine, dried over anhydrous sodium sulfate and filtered through diatomaceous earth. The mother liquor is evaporated to dryness giving a brownish residue. The residue is Kugelrohr-distilled to give 16.56 grams of colorless liquid at 45° C./0.3 mm which is essentially identical with the authentic product.

EXAMPLE 2

4-Trimethylsilylethynyl-1-octyn-4-ol

To a stirred suspension of 1.29 grams of magnesium and 10 mg of mercuric chloride in 12 ml of ether is added 0.4 ml of propargyl bromide. The reaction is initiated after stirring at room temperature for a few minutes. The stirred mixture is cooled in an ice-water bath and a solution of 9.64 grams of n-butyl trimethylsilylethynyl ketone and 3.51 ml of propargyl bromide in 13 ml of ether added dropwise so that the mixture is very gently boiling during a period of about 40 minutes. After addition is complete, the cooling bath is removed and the mixture is stirred at room temperature for about 1.5 hours. The mixture is recooled in an ice bath and 10 ml of saturated ammonium chloride solution is added. The resulting white mixture is filtered through diatomaceous earth. The clear mother liquor is washed with saturated sodium chloride solution and dried over anhydrous magnesium sulfate. The solvent is evaporated to dryness giving 10.5 grams of a red liquid. The liquid is Kugelrohr-distilled at 60° C./0.25-0.3 mm. The pale yellow liquid distillate which is the desired product weighed 8.5 grams.

EXAMPLE 3

4-Trimethylsilylethynyl-1-octyn-4-ol trimethylsilyl ether

To a stirred mixture of 8.5 grams of 4-trimethylsilylethynyl-1-octyn-4-ol and 6.2 grams of imidazole in 24 ml of dry dimethylformamide is added, under nitrogen, 5.7 ml of chlorotrimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness yielding 11.1 grams of the desired product.

EXAMPLE 4

4-Trimethylsilylethynyl-4-trimethylsiloxy-1-octen-1-tri-n-butyl stannane

To a mixture of 10 mg of azobisisobutyronitrile and 2.94 grams of 4-trimethylsilylethynyl-1-octyn-4-ol trimethylsilyl ether is added 2.65 ml of tri-n-butyl stannane via a syringe. The mixture is stirred and heated under nitrogen in an oil bath at 130° C. for about 3 hours and then cooled to room temperature. The mixture is vacum-distilled through a short-path distillation apparatus to remove a forerun at 40° C./0.4 mm. The yellow oil (pot residue) comprises the desired product.

EXAMPLE 5

15-Deoxy-16-hydroxy-16-trimethylsilylethynyl-PGE$_2$

A solution of 3.7 grams of 4-trimethylsilylethynyl-4-trimethylsiloxy-1-octen-1-tri-n-butyl stannane in 3 ml of tetrahydrofuran is cooled in a dry ice-acetone bath under nitrogen, treated with 6.4 mmol of n-butyl lithium during 10 minutes, stirred at −70° C. for 5 minutes, then at −40° C. for about one hour and finally at −40° C. to −30° C. for 30 minutes. Aliquots are quenched with water and assayed by NMR until the lithium exchange is shown to be complete which is after about 1.5 hours at −40° C. to −30° C.

A second mixture of 830 mg of copper pentyne, 2.55 grams of tri-n-butyl phosphene and 6 ml of ether is stirred at room temperature under nitrogen for about 20 minutes until a clear solution is obtained. The copper pentyne solution is transferred to the vinyl lithium solution (which is first recooled to −75° C. in a dry ice-acetone bath) via a syringe. After stirring at −75° C. for 2 hours, a solution of 2.1 grams of cyclopentenone-bis-TMS [U.S. Pat. No. 3,873,607 (Example 1125)] is added during 10 minutes. The mixture is stirred at −78° C. for 10 minutes, then at −50° C. to −40° C. for about one hour, then at −40° C. to −30° C. for 30 minutes and is then recooled to −50° C. The mixture is quenched by pouring it into a mixture of 200 ml of saturated ice-cold ammonium chloride solution and 100 ml of ether. The mixture is extracted with ethyl acetate. The combined ether-ethyl acetate extract is washed with water and brine. The solvents are evaporated to dryness. The residue is treated with 30 ml of acetic acid, 15 ml of tetrahydrofuran and 7.5 ml of water and stirred at room temperature under nitrogen for about 30 minutes. A 50 ml portion of toluene is added and the mixture is evaporated to dryness. The residue is applied to 12 grams of silica gel and then washed with 75 ml of hexane. The silica gel cake is washed with 150 ml of ethyl acetate. The ethyl acetate extract is passed through a dry 2 inch×50 inch column of 610 grams of silica gel and eluted with 450 ml of 70% ethyl acetate:1% acetic acid in hexane. The product is then eluted from the silica gel with ethyl acetate. The solvent is evaporated to dryness in the presence of toluene giving a total of 860 mg of the desired product.

EXAMPLE 6

15-Deoxy-16-hydroxy-16-ethynyl-PGE$_2$

To a solution of 300 mg of 15-deoxy-16-hydroxy-16-trimethylsilylethynyl-PGE$_2$ in 1.2 ml of methanol is added dropwise a solution of 2.7 grams of silver nitrate in 6 ml of water and 18 ml of ethanol. The mixture is then stirred at room temperature under nitrogen for one hour. One ml of a solution of one gram of potassium cyanide in 1.5 ml of water is added and the mixture stirred at room temperature for about 40 minutes. Water is added to dissolve the resulting white precipitate and the solution is neutralized with 5% hydrochloric acid. The white solid which formed is removed. The mother liquor is extracted with ether-ethyl acetate and the organic phase is washed with water and brine, filtered and then evaporated to dryness. The residue is purified through a 200 gram silica gel column (1 3/16 inch×45 inch) and is eluted with 70% ethyl acetate:1% acetic acid in hexane. The product fraction is eluted from the column with ethyl acetate. The solvent is evaporated to dryness in the presence of toluene yielding 240 mg of the desired product as an oiy residue.

EXAMPLES 7–9

Treatment of the acid chlorides of Table 1 by the procedure of Example 1 with bis-trimethylsilylacetylene is productive of the ketones of Table 1.

TABLE 1

| Example | Starting Acid Chloride | Product Alkyl Trimethyl-silylethynyl Ketone |
| --- | --- | --- |
| 7 | butyryl chloride | n-propyl trimethylsilyl-ethynyl ketone |
| 8 | hexanoyl chloride | n-pentyl trimethylsilyl-ethynyl ketone |
| 9 | heptanoyl chloride | n-hexyl trimethylsilyl-ethynyl ketone |

EXAMPLES 10–12

Treatment of the ketones of Table 2 by the procedure of Example 3 produces the 4-trimethylsilylethynyl-1-alkyn-4-ol's of the Table.

TABLE 2

| Example | Starting Ketone | Product 4-Trimethylsilyl-ethynyl-1-alkyn-4-ol |
| --- | --- | --- |
| 10 | 7 | 4-trimethylsilylethynyl-1-heptyn-4-ol |
| 11 | 8 | 4-trimethylsilylethynyl-1-nonyl-4-ol |
| 12 | 9 | 4-trimethylsilylethynyl-1-decyn-4-ol |

EXAMPLES 13–15

Treatment of the alkyn-4-ol's of Table 3 with chlorotrimethylsilane by the procedure of Example 3 followed by treatment of the resulting trimethylsilylether with tri-n-butylstannane by the procedure of Example 4 produces the alkenes of the Table.

TABLE 3

| Example | Starting Alkyn-4-ol | Product Alkene |
| --- | --- | --- |
| 13 | 10 | (E) 4-trimethylsilylethynyl-4-trimethylsiloxy-1-tri-n-butylstannane-1-heptene |
| 14 | 11 | (E) 4-trimethylsilylethynyl-4-trimethylsiloxy-1-tri-n-butylstannane-1-nonene |
| 15 | 12 | (E) 4-trimethylsilylethynyl-4-trimethylsiloxy-1-tri-n-butylstannane-1-decene |

EXAMPLE 16

Preparation of 4-Trimethylsiloxy-1-octyne

To a cold solution of 166 grams of 4-hydroxy-1-octyne [Prostaglandins, 10, 289 (1975)], and 240 grams of imidazole in one liter of dimethylformamide is added dropwise 202 grams of chlorotrimethylsilane. The mixture is allowed to stand at room temperature for about 2 to 3 days. The mixture is partitioned with water and hexane. The hexane layer is washed with brine, dried over magnesium sulfate, and concentrated. Distillation of the residue gives a colorless liquid, b.p. 38° (0.2 mm).

EXAMPLE 17

Preparation of 1-Iodo-4-trimethylsiloxy-trans-1-octene

To a stirred solution of 0.20 moles of freshly prepared bis-(3-methyl-2-butyl)borane in 300 ml of tetrahydrofuran at 0°–5° C. is added dropwise a solution of 19.8 grams of 4-trimethylsiloxy-1-octyne in 30 ml of tetrahydrofuran. The resulting mixture is stirred at ambient temperature for several hours, cooled in an ice bath, and treated with 53 grams of trimethylamine oxide. The mixture is stirred several hours at 25°–40° C. and then poured into 2 liters of 15% sodium hydroxide. The resulting mixture is treated immediately with a solution of 140 grams of iodine in 300 ml of tetrahydrofuran. After about 0.5 hour the organic phase is separated; then the aqueous phase is extracted with ether. The combined organic layers are washed with water, sodium thiosulfate solution, and brine; dried over magnesium sulfate; and concentrated to give an oil, pmr spectrum (CDCl$_3$): 6.2 (d, IC$\underline{H}$=) and 6.7 (quintuplet, =C$\underline{H}$—).

EXAMPLE 18

Preparation of 4-Hydroxy-1-iodo-trans-1-octene

A 23 grams portion of 1-iodo-4-trimethylsiloxy-trans-1=octene is dissolved in a mixture of 200 ml of glacial acetic acid, 100 ml of tetrahydrofuran, and 50 ml of water. After solution occurs, toluene is added and the mixture is evaporated. The resulting oil is chromatographed on silica gel with hexane progressively enriched in benzene followed by acetone to give 16 grams of an oil, pmr spectrum (CDCl$_3$):3.69 (m, C$\underline{H}$OH) and 2.3 (s, O$\underline{H}$).

EXAMPLE 19

Preparation of 4-Oxo-1-iodo-trans-1-octene

To a stirred suspension of 6.15 g of pyridinium chlorochromate (*Tetrahedron Letters*, 1975, 2647) in 20 ml of methylene chloride is added 450 mg of sodium acetate. After 5 minutes, a solution of 3.64 grams of 4-hydroxy-1-iodo-trans-1-octne in 15 ml of methylene chloride is added to one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give an orange liquid, pmr spectrum (CDCl$_3$):3.20 (d, j=7 cps, =CHC$\underline{H}_2$CO).

EXAMPLE 20

Preparation of 4-Hydroxy-4-(1-propynyl)-1-iodo-trans-1-octene

To a stirred solution of propynyllithium at −25° is added a solution of 4-oxo-1-iodo-trans-1-octene in tetrahydrofuran. After the addition, the solution is stirred at −20° to −15° C. for 30 minutes. The reaction is quenched with a mixture of hexane and ice. The aqueous phase is separated and extracted with additional hexane. The combined hexane extracts is washed successively with water and brine. The solution is dried over magnesium sulfate and concentrated. The residue is chromatographed on a silica gel column and is eluted with toluene to provide the product as an oil.

EXAMPLE 21

Preparation of 4-Hydroxy-4-(1-propynyl)-1-iodo-trans-1-decene

Treatment of 4-hydroxy-1-decyne (U.S. Pat. No. 3,950,406) by the procedures of Examples 16, 17, 18, 19 and 20 produces the iodo-decene compound.

EXAMPLES 22–23

Treatment of the iodoalkenes of Table 4 with chlorotrimethylsilane by the procedure of Example 3 produces the trimethylsilylethers of the Table.

TABLE 4

| Example | Starting Iodo alkene | Product Silylether |
|---|---|---|
| 22 | 20 | 4-trimethylsilyloxy-4-(1-propynyl)-1-iodo-trans-1-octene |
| 23 | 21 | 4-trimethylsilyloxy-4-(1-propynyl)-1-iodo-trans-1-decene |

EXAMPLE 24–95

Treatment of the vinylstannyl or iodoalkene derivatives of Example 4, Table 3 and Table 4, with n-butyllithium by the procedure of Example 5, followed by cuprate formation according to Example 5, followed by treatment of the cuprate with the cyclopentenone of Table 5 according to the procedure of Example 5, is productive of the prostanoids of Table 5.

EXAMPLES 96–143

Treatment of the 9-oxo-11α,16-dihydroxy-16-trimethylsilylethynyl-prostanoids of Table 6 by the procedure of Example 6 produces the corresponding 9-oxo-11α,16-dihydroxy-16-ethynyl-prostanoid of Table 6.

TABLE 5

| Example | Starting Cyclopentenone | Vinylstannyl Derivative | Product Prostanoid |
|---|---|---|---|
| 24 | 4-trimethylsilyloxy-2-(6-carbotrimethylsilyloxyhexyl)-cyclopent-2-en-1-one | 4 | 11α,16-dihydroxy-9-oxo-16-(trimethylsilylethynyl)-13-trans-prostenoic acid |
| 25 | 4-trimethylsilyloxy-2-(6-carbotrimethylsilyloxy-2-cis-hexenyl)-cyclopent-2-en-1-one | 4 | 11α,16-dihydroxy-9-oxo-16-(trimethylsilyethynyl)-5-cis, 13-trans-prostadienoic acid |
| 26 | 4-trimethylsilyloxy-2-(6-carbotrimethylsilyloxy-5-thiahexyl)-cyclopent-2-en-1-one | 4 | 11α,16-dihydroxy-9-oxo-16-(trimethylsilylethynyl)-3-thia-13-trans-prostenoic acid. |
| 27 | 4-trimethylsilyloxy-2-(6-carbotrimethylsilyloxy-5-oxahexyl)-cyclopent-2-en-1-one | 4 | 11α,16-dihydroxy-9-oxo-16-(trimethylsilylethynyl)-3-oxa-13-trans-prostenoic acid |
| 28 | 2-(6-carbomethoxyhexyl)-cyclopent-2-en-1-one | 4 | methyl-16-hydroxy-9-oxo-16-(trimethylsilylethynyl)-13-trans-prostenoate |
| 29 | 2-(6-carbethoxy-2-cis-hexenyl)-cyclopent- | 4 | ethyl-16-hydroxy-9-oxo-16-(trimethylsilylethynyl)5-cis, |

TABLE 5-continued

| | | |
|---|---|---|
| 30 | 2-en-1-one<br>2-(6-carbethoxy-5-thiahexyl)-cyclopent-2-en-1-one | 4 |
| 31 | 2-(6-carbethoxy-5-oxahexyl)-cyclopent-2-en-1-one | 4 |
| 32 | d-4-trimethylsilyloxy-2-(6-carbomethoxy-2-cis-hexenyl)-cyclopent-2-en-1-one | 4 |
| 33 | d-4-trimethylsilyloxy-2-(6-carbomethoxy-hexyl)-cyclopent-2-en-1-one | 4 |
| 34 | 4-(1-ethoxyethoxy)-2-[7-(1-ethoxyethoxy)-heptyl]-cyclopent-2-en-1-one | 4 |
| 35 | 4-(1-methoxy-1-methylethoxy)-2-[ 7-(1-methoxy-1-methylethoxy)-2-cis-heptenyl]-cyclopent-2-en-1-one | 4 |
| 36 | 4-methylsilyloxy-2-(6-carbotrimethylsilyloxy-hexyl)-cyclopent-2-en-1-one | 13 |
| 37 | 4-methylsilyloxy-2-(6-carbotrimethylsilyloxy-2-cis-hexenyl)-cyclopent-2-en-1-one | 13 |
| 38 | 4-methylsilyloxy-2-(6-carbotrimethyl-5-thia-hexyl)-cyclopent-2-en-1-one | 13 |
| 39 | 4-methylsilyloxy-2-(6-carbotrimethyl-5-oxa-hexyl)-cyclopent-2-en-1-one | 13 |
| 40 | 2-(6-carbomethoxyhexyl)-cyclopent-2-en-1-one | 13 |
| 41 | 2-(6-carbethoxy-2-cis-hexenyl)-cyclopent-2-en-1-one | 13 |
| 42 | 2-(6-carbethoxy-5-thiahexyl)-cyclopent-2-en-1-one | 13 |
| 43 | 2-(6-carbethoxy-5-oxahexyl)-cyclopent-2-en-1-one | 13 |
| 44 | d-4-trimethylsilyloxy-2-(6-carbomethoxy-2-cis-hexenyl)-cyclopent-2-en-1-one | 13 |
| 45 | d-4-trimethylsilyloxy-2-(6-carbomethoxy-hexyl)-cyclopent-2-en-1-one | 13 |
| 46 | 4-(1-ethoxyethoxy)-2-[7-(1-ethoxyethoxy)-heptyl]-cyclopent-2-en-1-one | 13 |
| 47 | 4-(1-methoxy-1-methylethoxy)-2-[7-(1-methyl-1-methylethoxy)-2-cis-heptenyl]-cyclopent-2-en-1-one | 13 |
| 48 | 4-trimethylsilyloxy-2-(6-carbotrimethyl-silyloxyhexyl)-cyclopent-2-en-1-one | 14 |
| 49 | 4-trimethylsilyloxy-2-(6-carbotrimethyl-silyloxy-2-cis-hexenyl)-cyclopent-2-en-1-one | 14 |
| 50 | 4-trimethylsilyloxy-2-(6-carbotrimethyl-silyloxy-5-thiahexyl)-cyclopent-2-en-1-one | 14 |
| 51 | 4-trimethylsilyloxy-2-(6-carbotrimethyl-silyloxy-5-oxahexyl)-cyclopent-2-en-1-one | 14 |
| 52 | 2-(6-carbomethoxyhexyl)-cyclopent-2-en-1-one | 14 |
| 53 | 2-(6-carbethoxy-2-cis-hexenyl)-cyclopent-2-en-1-one | 14 |
| 54 | 2-(6-carbethoxy-5-thiahexyl)-cyclopent-2-en-1-one | 14 |
| 55 | 2-(6-carbethoxy-5-oxahexyl)-cyclopent-2-en-1-one | 14 |
| 56 | d-4-trimethylsilyloxy-2-(6-carbomethoxy-2-cis-hexenyl)-cyclopent-2-en-1-one | 14 |
| 57 | d-4-trimethylsilyloxy-2-(6-carbomethoxy-hexyl)-cyclopent-2-en-1-one | 14 |
| 58 | 4-(1-ethoxyethoxy)-2-[7-(1-ethoxyethoxy)-heptyl]-cyclopent-2-en-1-one | 14 |
| 59 | 4-(1-methoxy-1-methylethoxy)-2-[7-(1-methoxy-1-methylethoxy)-2-cis-heptenyl]-cyclopent-2-en-1-one | 14 |
| 60 | 4-trimethylsilyloxy-2-(6-carboxymethylsilyl-oxyhexyl)-cyclopent-2-en-1-one | 15 |
| 61 | 4-trimethylsilyloxy-2-(6-carboxytrimethyl-silyloxy-2-cis-hexenyl)-cyclopent-2-en-1-one | 15 |
| 62 | 4-trimethylsilyloxy-2-(6-carboxytrimethyl-silyloxy-5-thiahexyl)-cyclopent-2-en-1-one | 15 |
| 63 | 4-trimethylsilyloxy-2-(6-carboxytrimethyl-silyloxy-5-oxahexyl)-cyclopent-2-en-1-one | 15 |
| 64 | 2-(6-carbomethoxyhexyl)-cyclopent-2-en-1-one | 15 |
| 65 | 2-(6-carbethoxy-2-cis-hexenyl)-cyclopent-2-en-1-one | 15 |
| 66 | 2-(6-carbethoxy-5-thiahexyl)-cyclopent-2-en-1-one | 15 |
| 67 | 2-(6-carbethoxy-5-oxahexyl)-cyclopent-2-en-1-one | 15 |
| 68 | d-trimethylsilyloxy-2-(6-carbomethoxy-cis-hexenyl)-cyclopent-2-en-1-one | 15 |

| | |
|---|---|
| | 13-trans-prostenoic acid |
| | ethyl-16-hydroxy-9-oxo-16-(trimethylsilylethynyl)-3-thia-13-trans-prostenoate |
| | ethyl-16-hydroxy-9-oxo-16-(trimethylsilylethynyl)-3-oxa-13-trans-prostenoate |
| | nat-methyl-11α,16-dihydroxy-9-oxo-16-(trimethylsilylethynyl)-5-cis,13-trans-prostadienoate |
| | nat-methyl-11α,16-dihydroxy-9-oxo-16-(trimethylsilylethynyl)-13-trans-prostenoate |
| | 1,11α,16-trihydroxy-9-oxo-16-(trimethylsilylethynyl)-13-trans-prostene |
| | 1,11α,16-trihydroxy-9-oxo-16-(trimethylsilylethynyl)-5-cis,13-trans-prostadiene |
| | 11α,16-dihydroxy-9-oxo-16-(trimethylsilylethynyl)-20-nor-13-trans-prostenoic acid |
| | 11α,16-dihydroxy-9-oxo-16-(trimethylsilylethynyl)-20-nor-5-cis,13-trans-prostadienoic acid |
| | 11α,16-dihydroxy-9-oxo-16-(trimethylsilylethynyl)-20-nor-3-thia-13-trans-prostenoic acid |
| | 11α,16-dihydroxy-9-oxo-16-(trimethylsilylethynyl)-20-nor-3-oxa-13-trans-prostenoic acid |
| | methyl-16-hydroxy-9-oxo-16-(trimethylsilylethynyl)-20-nor-13-trans-prostenoate |
| | ethyl-16-hydroxy-9-oxo-16-(trimethylsilylethynyl)-20-nor-5-cis,13-trans-prostadienoate |
| | ethyl-16-hydroxy-9-oxo-16-(trimethylsilylethynyl)-20-nor-3-thia-13-trans-prostenoate |
| | ethyl-16-hydroxy-9-oxo-16-(trimethylsilylethynyl)-20-nor-3-oxa-13-trans-prostenoate |
| | nat-methyl-11α,16-dihydroxy-9-oxo-16-(trimethylsilylethynyl)-20-nor-5-cis,13-trans-prostadienoate |
| | nat-methyl-11α,16-dihydroxy-9-oxo-16-(trimethylsilylethynyl)-20-nor-13-trans-prostenoate |
| | 1,11α,16-trihydroxy-9-oxo-16-(trimethylsilylethynyl)-20-nor-13-trans-prostene |
| | 1,11α,16-trihydroxy-9-oxo-16-(trimethylsilylethynyl)-20-nor-5-cis,13-trans-prostadiene |
| | 11α,16-dihydroxy-9-oxo-16-(trimethylsilylethynyl)-20-homo-trans-prostenoic acid |
| | 11α,16-dihydroxy-9-oxo-16-(trimethylsilylethynyl)-20-homo-5-cis,13-trans-prostadienoic acid |
| | 11α,16-dihydroxy-9-oxo-16-(trimethylsilylethynyl)-20-homo-3-thia-13-trans-prostenoic acid |
| | 11α,16-dihydroxy-9-oxo-16-(trimethylsilylethynyl)-20-homo-3-oxa-13-trans-prostenoic acid |
| | methyl-16-hydroxy-9-oxo-16-(trimethylsilylethynyl)-20-homo-13-trans-prostenoate |
| | ethyl-16-hydroxy-9-oxo-16-(trimethylsilylethynyl)-20-homo-5-cis,13-trans-prostadienoate |
| | ethyl-16-hydroxy-oxo-16-(trimethylsilylethynyl)-20-homo-3-thia-13-trans-prostenoate |
| | ethyl-16-hydroxy-9-oxo-16-(trimethylsilylethynyl)-20-homo-3-oxa-13-trans-prostenoate |
| | nat-11α,16-dihydroxy-9-oxo-16-(trimethylsilylethynyl)-20-homo-5-cis,13-trans-prostadienoate |
| | nat-11α,16-dihydroxy-9-oxo-16-(trimethylsilylethynyl)-20-homo-13-trans-prostenoate |
| | 1,11α,16-trihydroxy-9-oxo-16-(trimethylsilylethynyl)-20-homo-13-trans-prostene |
| | 1,11α,16-trihydroxy-9-oxo-16-(trimethylsilylethynyl)-20-homo-5-cis,13-trans-prostadiene |
| | 11α,16-dihydroxy-9-oxo-16-(trimethylsilylethynyl)-20-ethyl-13-trans-prostenoic acid |
| | 11α,16-dihydroxy-9-oxo-16-(trimethylsilylethynyl)-20-ethyl-5-cis,13-trans-prostadienoic acid |
| | 11α,16-dihydroxy-9-oxo-16-(trimethylsilylethynyl)-20-ethyl-3-thia-13-trans-prostenoic acid |
| | 11α,16-dihydroxy-9-oxo-16-(trimethylsilylethynyl)-20-ethyl-3-oxa-13-trans-prostenoic acid |
| | methyl-16-hydroxy-9-oxo-16-(trimethylsilylethynyl)-20-ethyl-13-trans-prostenoate |
| | ethyl-16-hydroxy-9-oxo-16-(trimethylsilylethynyl)-20-ethyl-5-cis,13-trans-prostadienoate |
| | ethyl-16-hydroxy-9-oxo-16-(trimethylsilylethynyl)-20-ethyl-3-thia-13-trans-prostenoate |
| | ethyl-16-hydroxy-9-oxo-16-(trimethylsilylethynyl)-20-ethyl-3-oxa-13-trans-prostenoate |
| | nat-methyl-11α,16-dihydroxy-9-oxo-16-(trimethylsilylethynyl)-20-ethyl-5-cis,13-trans-prostadienoate |

TABLE 5-continued

| | | | |
|---|---|---|---|
| 69 | d-trimethylsilyloxy-2-(6-carbomethoxyhexyl)-cyclopent-2-en-1-one | 15 | nat-methyl-11α,16-dihydroxy-9-oxo-16-(trimethylsilylethynyl)-20-ethyl-13-trans-prostenoate |
| 70 | 4-(1-ethoxyethoxy)-2-[7-(1-ethoxyethoxy)-heptyl]-cyclopent-2-en-1-one | 15 | 1,11α,16-trihydroxy-9-oxa-16-(trimethylsilylethynyl)-20-ethyl-13-trans-prostene |
| 71 | 4-(1-methoxy-1-methylethoxy)-2-[7-(1-methyl-1-methylethoxy)-2-cis-heptenyl]-cyclopent-2-en-1-one | 15 | 1,11α,16-trihydroxy-9-oxo-16-(trimethylsilylethynyl)-20-ethyl-5-cis,13-trans-prostadiene |

| Example | Starting Cyclopentenone | Iodoalkene Derivative | Product Prostanoid |
|---|---|---|---|
| 72 | 4-trimethylsilyloxy-2-(6-carbotrimethylsilyloxyhexyl)-cyclopent-2-en-1-one | 22 | 11α,16-dihydroxy-9-oxo-16-(1-propynyl)-13-trans-prostenoic acid |
| 73 | 4-trimethylsilyloxy-2-(6-carbotrimethyl-silyloxy-2-cis-hexenyl)-cyclopent-2-en-1-one | 22 | 11α,16-dihydroxy-9-oxo-16-(1-propynyl)-5-cis,13-trans-prostadienoic acid |
| 74 | 4-trimethylsilyloxy-2-(6-carbotrimethyl-silyloxy-5-thiahexyl)-cyclopent-2-en-1-one | 22 | 11α,16-dihydroxy-9-oxo-16-(1-propynyl)-3-thia-13-trans-prostenoic acid |
| 75 | 4-trimethylsilyloxy-2-(6-carbotrimethyl-silyloxy-5-oxahexyl)-cyclopent-2-en-1-one | 22 | 11α,16-dihydroxy-9-oxo-16-(1-propynyl)-3-oxa-13-trans-prostenoic acid |
| 76 | 2-(6-carbomethoxyhexyl)-cyclopent-2-en-1-one | 22 | methyl-16-hydroxy-9-oxo-16-(1-propynyl)-13-trans-prostenoate |
| 77 | 2-(6-carbethoxy-2-cis-hexenyl)-cyclopent-2-en-1-one | 22 | ethyl-16-hydroxy-9-oxo-16-(1-propynyl)-5-cis,13-trans-prostadienoate |
| 78 | 2-(6-carbethoxy-5-thiahexyl)-cyclopent-2-en-1-one | 22 | ethyl-16-hydroxy-9-oxo-16-(1-propynyl)-3-thia-13-trans-prostenoate |
| 79 | 2-(6-carbethoxy-5-oxahexyl)-cyclopent-2-en-1-one | 22 | ethyl-16-hydroxy-9-oxo-16-(1-propynyl)-3-oxa-13-trans-prostenoate |
| 80 | d-4-trimethylsilyloxy-2-(6-carbomethoxy-2-cis-hexenyl)-cyclopent-2-en-1-one | 22 | nat-methyl-11α,16-dihydroxy-9-oxo-16-(1-propynyl)-5-cis,13-trans-prostadienoate |
| 81 | d-4-trimethylsilyloxy-2-(6-carbomethoxyhexyl)-cyclopent-2-en-1-one | 22 | nat-methyl-11α,16-dihydroxy-9-oxo-16-(1-propynyl)-13-trans-prostenoate |
| 82 | 4-(1-ethoxyethoxy)-2-[7-(1-ethoxyethoxy)-heptyl]-cyclopent-2-en-1-one | 22 | 1,11α,16-trihydroxy-9-oxo-16-(1-propynyl)-13-trans-prostene |
| 83 | 4-(1-methoxy-1-methoxyethoxy)-2-[7-(1-methoxy-1-methoxyethoxy)-2-cis-heptenyl]-cyclopent-2-en-1-one | 22 | 1,11α,16-trihydroxy-9-oxo-16-(1-propynyl)-5-cis,13-trans-prostadiene |
| 84 | 4-trimethylsilyloxy-2-(6-carbotrimethyl-silyloxyhexyl)-cyclopent-2-en-1-one | 23 | 11α,16-dihydroxy-9-oxo-16-(1-propynyl)-20-ethyl-13-trans-prostenoic acid |
| 85 | 4-trimethylsilyloxy-2-(6-carbotrimethyl-silyloxy-2-cis-hexenyl)-cyclopent-2-en-1-one | 23 | 11α,16-dihydroxy-9-oxo-16-(1-propynyl)-20-ethyl-5-cis,13-trans-prostadienoic acid |
| 86 | 4-trimethylsilyloxy-2-(6-carbotrimethyl-silyloxy-5-thiahexyl)-cyclopent-2-en-1-one | 23 | 11α,16-dihydroxy-9-oxo-16-(1-propynyl)-20-ethyl-3-thia-13-trans-prostenoic acid |
| 87 | 4-trimethylsilyloxy-2-(6-carbotrimethyl-silyloxy-5-oxahexyl)-cyclopent-2-en-1-one | 23 | 11α,16-dihydroxy-9-oxo-16-(1-propynyl)-20-ethyl-3-oxa-13-trans-prostenoic acid |
| 88 | 2-(6-carbomethoxyhexyl)-cyclopent-2-en-1-one | 23 | methyl-16-hydroxy-9-oxo-16-(1-propynyl)-20-ethyl-13-trans-prostenoate |
| 89 | 2-(6-carbethoxy-2-cis-hexenyl)-cyclopent-2-en-1-one | 23 | ethyl-16-hydroxy-9-oxo-16-(1-propynyl)-20-ethyl-5-cis,13-trans-prostadienoate |
| 90 | 2-(6-carbethoxy-5-thiahexyl)-cyclopent-2-en-1-one | 23 | ethyl-16-hydroxy-9-oxo-16-(1-propynyl)-20-ethyl-3-thia-13-trans-prostenoate |
| 91 | 2-(6-carbethoxy-5-oxahexyl)-cyclopent-2-en-1-one | 23 | ethyl-16-hydroxy-9-oxo-16-(1-propynyl)-20-ethyl-3-oxa-13-trans-prostenoate |
| 92 | d-4-trimethylsilyloxy-2-(6-carbomethoxy-2-cis-hexenyl)-cyclopent-2-en-1-one | 23 | nat-methyl-11α,16-dihydroxy-9-oxo-16-(1-propynyl)-20-ethyl-5-cis,13-trans-prostadienoate |
| 93 | d-4-trimethylsilyloxy-2-(6-carbomethoxyhexyl)-cyclopent-2-en-1-one | 23 | nat-methyl-11α,16-dihydroxy-9-oxo-16-(1-propynyl)-20-ethyl-13-trans-prostenoate |
| 94 | 4-(1-ethoxyethoxy)-2-[7-(1-ethoxyethoxy)-heptyl]-cyclopent-2-en-1-one | 23 | 1,11α,16-trihydroxy-9-oxo-16-(1-propynyl)-20-ethyl-13-trans-prostene |
| 95 | 4-(1-methoxy-1-methylethoxy)-2-[7-(1-methoxy-1-methylethoxy)-2-cis-heptenyl]-cyclopent-2-en-1-one | 23 | 1,11α,16-trihydroxy-9-oxo-16-(1-propynyl)-20-ethyl-5-cis,13-trans-prostadiene |

TABLE 6

| Example | Starting Prostanoid | Product Prostanoid |
|---|---|---|
| 96 | 24 | 11α,16-dihydroxy-9-oxo-16-ethynyl-13-trans-prostenoic acid |
| 97 | 25 | 11α,16-dihydroxy-9-oxo-16-ethynyl-5-cis,13-trans-prostadienoic acid |
| 98 | 26 | 11α,16-dihydroxy-9-oxo-16-ethynyl-3-thia-13-trans-prostenoic acid |
| 99 | 27 | 11α,16-dihydroxy-9-oxo-16-ethynyl-3-oxa-13-trans-prostenoic acid |
| 100 | 28 | methyl-16-hydroxyl-9-oxo-16-ethynyl-13-trans-prostenoate |
| 101 | 29 | ethyl-16-hydroxyl-9-oxo-16-ethynyl-5-cis,13-trans-prostadienoate |
| 102 | 30 | ethyl-16-hydroxyl-9-oxo-16-ethynyl-3-thia-13-trans-prostenoate |
| 103 | 31 | ethyl-16-hydroxyl-9-oxo-16-ethynyl-3-oxa-13-trans-prostenoate |
| 104 | 32 | nat-methyl-11α,16-dihydroxy-9-oxo-16-ethynyl-5-cis, |

TABLE 6-continued

| Example | Starting Prostanoid | Product Prostanoid |
|---|---|---|
| 105 | 33 | 13-trans-prostadienoate<br>nat-methyl-11α,16-dihydroxy-9-oxo-16-ethynyl-13-trans-prostenoate |
| 106 | 34 | 1,11α,16-trihydroxy-9-oxo-16-ethynyl-13-trans-prostene |
| 107 | 35 | 1,11α,16-trihydroxy-9-oxo-16-ethynyl-5-cis,13-trans-prostadiene |
| 108 | 36 | 11α,16-dihydroxy-9-oxo-16-ethynyl-20-nor-13-trans-prostenoic acid |
| 109 | 37 | 11α,16-dihydroxy-9-oxo-16-ethynyl-20-nor-5-cis,13-trans-prostadienoic acid |
| 110 | 38 | 11α,16-dihydroxy-9-oxo-16-ethynyl-20-nor-3-thia-13-trans-prostenoic acid |
| 111 | 39 | 11α,16-dihydroxy-9-oxo-16-ethynyl-20-nor-3-oxa-13-trans-prostenoic acid |
| 112 | 40 | methyl-16-hydroxy-9-oxo-16-ethynyl-20-nor-13-trans-prostenoate |
| 113 | 41 | ethyl-16-hydroxy-9-oxo-16-ethynyl-20-nor-5-cis,13-trans-prostadienoate |
| 114 | 42 | ethyl-16-hydroxy-9-oxo-16-ethynyl-20-nor-3-thia-13-trans-prostenoate |
| 115 | 43 | ethyl-16-hydroxy-9-oxo-16-ethynyl-20-nor-3-oxa-13-trans-prostenoate |
| 116 | 44 | nat-methyl-11α,16-dihydroxy-9-oxo-16-ethynyl-20-5-cis,13-trans-prostadienoate |
| 117 | 45 | nat-methyl-11α,16-dihydroxy-9-oxo-16-ethynyl-20-nor-13-trans-prostenoate |
| 118 | 46 | 1,11α,16-trihydroxy-9-oxo-16-ethynyl-20-nor-13-trans-prostene |
| 119 | 47 | 1,11α,16-trihydroxy-9-oxo-16-ethynyl-20-nor-5-cis,13-trans-prostadiene |
| 120 | 48 | 11α,16-dihydroxy-9-oxo-16-ethynyl-20-homo-13-trans-prostenoic acid |
| 121 | 49 | 11α,16-dihydroxy-9-oxo-16-ethynyl-20-homo-5-cis,13-trans-prostadienoic acid |
| 122 | 50 | 11α,16-dihydroxy-9-oxo-16-ethynyl-20-homo-3-thia-13-trans-prostenoic acid |
| 123 | 51 | 11α,16-dihydroxy-9-oxo-16-ethynyl-20-homo-3-oxa-13-trans-prostenoic acid |
| 124 | 52 | methyl-16-hydroxy-9-oxo-16-ethynyl-20-homo-13-trans-prostenoate |
| 125 | 53 | ethyl-16-hydroxy-9-oxo-16-ethynyl-20-homo-5-cis,13-trans-prostadienoate |
| 126 | 54 | ethyl-16-hydroxy-9-oxo-16-ethynyl-20-homo-3-thia-13-trans-prostenoate |
| 127 | 55 | ethyl-16-hydroxy-9-oxo-16-ethynyl-20-homo-3-oxa-13-trans-prostenoate |
| 128 | 56 | nat-methyl-11α,16-dihydroxy-9-oxo-16-ethynyl-20-homo-5-cis,13-trans-prostadienoate |
| 129 | 57 | nat-methyl-11α,16-dihydroxy-9-oxo-16-ethynyl-20-homo-13-trans-prostenoate |
| 130 | 58 | 1,11α,16-trihydroxy-9-oxo-16-ethynyl-20-homo-13-trans-prostene |
| 131 | 59 | 1,11α,16-trihydroxy-9-oxo-16-ethynyl-20-homo-13-trans-prostadiene |
| 132 | 60 | 11α,16-dihydroxy-9-oxo-16-ethynyl-20-ethyl-13-trans-prostenoic acid |
| 133 | 61 | 11α,16-dihydroxy-9-oxo-16-ethynyl-20-ethyl-5-cis,13-trans prostadienoic acid |
| 134 | 62 | 11α,16-dihydroxy-9-oxo-16-ethynyl-20-ethyl-3-thia-13-trans-prostenoic acid |
| 135 | 63 | 11α,16-dihydroxy-9-oxo-16-ethynyl-20-ethyl-3-oxa-13-trans-prostenoic acid |
| 136 | 64 | methyl-16-dihydroxy-9-oxo-16-ethynyl-20-ethyl-13-trans-prostenoate |
| 137 | 65 | ethyl-16-hydroxy-9-oxo-16-ethynyl-20-ethyl-5-cis,13-trans-prostadienoate |
| 138 | 66 | ethyl-16-hydroxy-9-oxo-16-ethynyl-20-ethyl-3-thia-13-trans-prostenoate |
| 139 | 67 | ethyl-16-hydroxy-9-oxo-16-ethynyl-20-ethyl-3-oxa-13-trans-prostenoate |
| 140 | 68 | nat-methyl-11α,16-dihydroxy-9-oxo-16-ethynyl-20-ethyl-5-cis,13-trans-prostadienoate |
| 141 | 69 | nat-methyl-11α,16-dihydroxy-9-oxo-16-ethynyl-20-ethyl-13-trans-prostenoate |
| 142 | 70 | 1,11α,16-trihydroxy-9-oxo-16-ethynyl-20-ethyl-13-trans-prostene |
| 143 | 71 | 1,11α,16-trihydroxy-9-oxo-16-ethynyl-20-ethyl-5-cis,13-trans-prostadiene |

EXAMPLE 144

TABLE 7

| Example | Starting Cyclopentenone | Product Ether |
|---|---|---|
| 148 | 2-(6-carboxyhexyl)-4-hydroxycyclopent-2- | 4-trimethylsiloxy-2-(6-carbotrimethylsiloxyhexyl)-cyclopent-2-en-1-one |
| 149 | 1-2-(6-carbomethoxy-hexyl)-4-hydroxycyclopent-2-en-1-one[2] | 1,4-trimethylsiloxy-2-(6-carbomethoxy)-cyclopent-2-en-1-one |
| 150 | 1-2-(6-carbomethoxy-2-cis-hexenyl)-4-hydroxycyclopent-2-en-1-one[3] | 1-4-trimethylsiloxy-2-(6-carbomethoxy-2-cis-hexenyl)cyclopent-2-en-1-one |
| 151 | 2-(6-carboxy-2-cisoctenyl)-4-hydroxycyclopent-2-en-1-one[4] | 2-(6-carbotrimethylsiloxy-2-cis-octenyl)-4-trimethylsiloxycyclopent-2-en-1-one |
| 152 | 2-(6-carboxy-5-oxahexyl)-4-hydroxycyclopent-2-en-1-one[4] | 4-trimethylsiloxy-2-(6-carbotrimethsiloxy-5-oxahexyl)-cyclopent-2-en-1-one |

References:
[1] U.S. Pat. No. 3,873,607
[2] Pappo, et al., Tetrahedron Letters, 943 (1973)
[3] Bruhn, et al., Ibid., 235 (1976)
[4] U.S. Pat. No. 3,950,406

Preparation of
9-oxo-16-hydroxy-16-(1-propynyl)-13-trans-prostenoic acid

A solution of 2 grams of methyl-16-hydroxy-9-oxo-16-(1-propynyl)-13-trans-prostenoic acid (Example 40) in 32 ml methanol water (1:1) containing 850 mg potassium hydroxide is stirred at ambient temperature for about 18 hours. The mixture is acidified with 10% hydrochloric acid; then the solution is extracted with ether several times. The ether extracts are combined, washed with a saturated sodium chloride solution, dried over anhydrous magnesium sulfate and taken to dryness to give an oil which is partly crystallized. Recrystallization of the oil from ether-hexane gives white crystals of the product compound.

EXAMPLE 145

Saponification of the remaining 9-oxo-16-hydroxy-16-ethynyl prostenoate, 9-oxo-16-hydroxy-16-ethynyl prostadienoate, 9-oxo-16-hydroxy-16-(1-propynyl)-prostenoate, and 9-oxo-16-hydroxy-16-(1-propynyl)-prostadienoate compounds disclosed by Examples 24 to 143 by the procedure described in Example 144 produces the corresponding 9-oxo-16-hydroxy-16-ethynyl-prostenoic, 9-oxo-16-hydroxy-16-ethynyl-prostadienoic, 9-oxo-16-hydroxy-16-(1-propynyl)-prostenoic, and 9-oxo-16-hydroxy-16-(1-propynyl)-prostadienoic acids.

EXAMPLE 146

Treatment of the free acid compounds disclosed by Examples 24–143 with diazomethane in ether produces the corresponding methyl esters.

EXAMPLE 147

Treatment of the free acid compounds disclosed by Examples 24–143 with diazohexane produces the corresponding hexyl esters.

EXAMPLES 148–152

Treatment of the carboxy-cyclopentenones or carbomethoxy-cyclopentenones of Table 7 with chlorotrimethylsilane by the procedure disclosed in U.S. Pat. No. 3,873,607 (Example 958), incorporated by reference herein, produces the corresponding bistrimethylsilylether ethyl esters or trimethylsilylether methyl esters of Table 7.

EXAMPLE 153

Preparation of
4-(1-ethoxyethoxy)-2-[7-(1-ethoxyethoxy)heptyl]cyclopent-2-en-1-one The 4-(1-ethoxyethoxy)-2-[7-(1-ethoxyethoxy)heptyl]cyclopent-2-en-1-one which is used to make the 1-hydroxy-13-trans-prostene compounds disclosed by Examples 24 to 143 is synthesized according to the procedure disclosed by Kluender et al. in Tetrahedron Letters, No. 24, pp. 2063–2066 (1977) which is incorporated by reference herein.

EXAMPLE 154

Preparation of
2,5-dihydro-2,5-dimethoxy-2-(8'-hydroxy-3'-cis-octenyl) furan

To a stirred solution of 10 ml of 3.6 m (70% solution) sodium bis-(2-methoxyethoxy) aluminum hydride in toluene is added a solution of 4.85 grams (18 m moles) of 2,5-dihydro-2,5-dimethoxy-2-(7'-carboxy-3'-cis-heptenyl) furan in 90 ml of toluene during a 60 minute time period, while maintaining a temperature of 75° C. After the addition is complete the mixture is heated at 75° C. for 2 hours. The mixture is then cooled to 0° C., is diluted with 50 ml of ether, and then 20 ml of 20% aqueous sodium hydroxide is added dropwise. The organic layer is separated, washed with brine and dried over anhydrous potassium carbonate. Evaporation of the solvent provides 2,5-dihydro-2,5-methoxy-2-(8'-hydroxy-3'-cis-octenyl)furan.

EXAMPLE 155

Preparation of
2-(7'-hydroxy-2'-cis-heptenyl)-4-hydroxycyclopent-2-en-1-one

A stirred solution of 5.12 grams (20 m moles) of 2,5-dihydro-2,5-dimethoxy-2-(8'-hydroxy-3'-cis-octenyl) furan (Example 154), 2.65 grams (19.2 m moles) of sodium dihydrogen phosphate monohydrate, 525 mg (16.4 m moles) of anhydrous sodium acetate, and 20 mg of hydroquinone in 135 ml dioxane and 68 ml water is heated at reflux temperature for 24 hours. The stirred solution is then cooled to 50° C. and 5.4 ml (0.1 moles)

of concentrated sulfuric acid is added in a dropwise manner. The resulting solution is stirred at reflux temperature for 18 hours, then is cooled to 25° C., saturated with sodium chloride, and extracted with ethyl acetate. The extract is washed with brine, dried over magnesium sulfate and concentrated to provide the product, 2-(7'hydroxy-2'cis-heptenyl)-4-hydroxycyclopent-2-en-1-one.

EXAMPLE 156

Preparation of 4-(1-methoxy-1-methylethoxy)-2-[7-(1-methoxy-1-methylethoxy)-2-cis-heptenyl]-cyclopent-2-en-1-one To a stirred solution of 2.10 grams (10 m moles) of 2-(7'-hydroxy-2'-cis-heptenyl)-4-hydroxycyclopent-2-en-1-one (Example 155) in 20 ml of dichloromethane, 3.6 ml of 2-methoxypropane and 0.015 ml of dichloroacetic acid are successively added at a temperature of about 25° C. After stirring three hours, the solution is diluted with hexane and washed with saturated sodium solution and brine. The solution is dried over anhydrous potassium carbonate, filtered and evaporated to provide the product, 4-(1-methoxy-1-methylethoxy)-2-[7-(1-methoxy-1-methylethoxy)-2-cis-heptenyl]-cyclopent-2-en-1-one.

EXAMPLE 157

Preparation of 5-Chloro-1-(2-furyl)-1-pentanol

To a stirred suspension of 2-furyllithium [prepared from 0.53 moles of n-butyllithium and 39.5 g of furan by the procedure of *J. Org. Chem.*, 27, 1216 (1962)] in 350 ml of ether and with 200 ml of hexane at $-78°$ C. is added a solution of 57.9 g of 5-chloropentanol [*Chem. Abstr.*, 59, 7579F (1963)] in 80 ml of ether over about 25 minutes. The mixture is warmed to 0° C. during 20 minutes, stirred at 0° C. for 15 minutes, and treated with 140 ml of saturated ammonium chloride. The ether phase is washed with water and brine, dried over magnesium sulfate and potassium carbonate mixture, and concentrated to give a liquid, pmr spectrum (CECl$_3$): $\delta$3.59 (triplet, C$\underline{H}_2$Cl) and 4.70 (triplet, CH$_2$CHOH).

EXAMPLE 158

Preparation of 5-(Carbethoxymethylthio)-1-(2-furyl)-1-pentanol

To a stirred, refluxing mixture of 76 g of ethyl mercaptoacetate, 79.5 g (Example 157), and 10 ml of 1.5 M sodium ethoxide in ethanol is added an additional 300 ml of 1.5 M sodium ethoxide over about 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): $\delta$3.24 (singlet, —SC$\underline{H}_2$CH$_3$) and 4.70 (triplet, CH$_2$C$\underline{H}$OH).

EXAMPLE 159

Preparation of 4-Hydroxy-2-[4-(carboxymethylthio)butyl]cyclopent-2-en-1-one

A stirred solution of 125 g of 5-(carbethoxymethylthio)-1-(2-furyl)-1-pentanol (Example 158), 22.4 g of sodium formate, 250 ml of formic acid, and 400 mg of hydroquinone in 2000 ml of dioxane and 1330 ml of water is refluxed for about 20 hours.

The solution, containing crude 3-hydroxy-2-[4-(carbethoxymethylthio)butyl]cyclopent-4-en-1-one, is cooled and treated during 10 minutes with 75 ml of sulfuric acid (d=1.84) with stirring. The stirred solution is refluxed for about 16 hours, cooled, saturated with sodium chloride, and extracted with ethyl acetate. The extract is washed with brine, dried over magnesium sulfate, and concentrated. The residue is chromatographed on silica gel and is eluted with chloroform progressively enriched in ether, ether, and ether progressively enriched in acetone to afford the subject compound as an oil; pmr spectrum (CDCl$_3$): $\delta$3.24 (singlet, —SC$\underline{H}_2$CH$_3$) 5.0 (broad singlet, —C$\underline{H}$OH—), and 7.38 (singlet, vinyl hydrogen).

EXAMPLE 160

Preparation of 2-[4-(Carbotrimethylsiloxymethylthio)butyl]-4-trimethylsiloxycyclopent-2-en-1-one To a stirred solution of 28.4 g of 4-hydroxy-2-[4-(carboxymethylthio)butyl]cyclopent-2-en-1-one (Example 159) and 76 ml of hexamethyldisilazone in 330 ml of pyridine at 5° C. is added 38 ml of chlorotrimethylsilane over 5 minutes. The mixture is stirred at ambient temperature for about 3.5 hours, at 45° C. for 5 minutes, and then evaporated to remove the solvent. The residue is stirred with 1000 ml of petroleum ether and filtered. The filtrate is treated with charcoal and filtered; the resulting filtrate is concentrated with the aid of toluene to give a liquid, pmr spectrum (CDCl$_3$): 0.18 (singlet, trimethylsiloxy group) and 0.28 (singlet, trimethylsiloxycarbonyl group).

EXAMPLE 161

Preparation of 9-oxo-16-hydroxyl-16-ethynyl-5-cis,10,13-trans-prostatrienoic acid To a stirred solution of 9-oxo-11,16-dihydroxy-16-ethynyl-5-cis,13-trans-prostadienoic acid (Example 97) in pyridine is added acetic anhydride. After standing for 5 hours at room temperature, the solution is stirred with a mixture of ethyl acetate and 1 M aqueous sodium bisulfate at about 0° C. The ethyl acetate layer is washed with brine and concentrated in the presence of toluene.

The residue, which consists of crude 9-oxo-11-acetoxy-16-hydroxy-16-ethynyl-5-cis,13-trans-prostadienoic acid, is dissolved in methanol with potassium acetate. After standing for about 18 hours at room temperature, the solution is partitioned with ethyl acetate and brine. The organic phase is washed with brine, dried over magnesium sulfate, and concentrated. The residue is purified by partition chromatography on Celite with the heptane-dichloromethane-methanol-water (80:20:15:6) system to give the product as an oil.

EXAMPLE 162

Treatment of the 9-oxo-11$\alpha$,16-dihydroxy compounds disclosed by Examples 24–147 with acetic anhydride in pyridine followed by potassium acetate in methanol according to the procedure disclosed by Example 161 furnishes the corresponding 9-oxo-16-hydroxy-$\Delta^{10}$compound (PGA derivative).

EXAMPLE 163

Preparation of
9α,11α,16-Trihydroxy-16-ethynyl-5-cis,13-trans-prostadienoic acid To a stirred solution of 9-oxo-11α,16-dihydroxy-16-ethynyl-5-cis,13-trans-prostadienoic acid (Example 97) in tetrahydrofuran at −70° is added a solution of lithium perhydro-9b-boraphenalyl hydride in tetrahydrofuran. The solution is stirred at −78° C. for 30 minutes, warmed to 0° C. during 15 minutes, and treated with water. The mixture is partitioned with ether-potassium carbonate solution. The aqueous phase is acidified with dilute hydrochloric acid and extracted with ethyl acetate. The extract is washed with water and brine, dried over magnesium sulfate, and concentrated. The resulting residue is subjected to dry column chromatography on silica gel with 1% acetic acid in ethyl acetate to provide a viscous oil.

EXAMPLE 164

Reduction of the 9-oxo-compounds disclosed by Examples 24–147 with lithium perhydro-9b-boraphenalyl hydride by the method described in Example 163 produces the corresponding 9α-hydroxy compounds (PGFα derivatives).

EXAMPLE 165

Preparation and separation of
9α,11α,16-Trihydroxy-16-ethynyl-5-cis-13-trans-prostadienoic acid and
9β,11α,16-trihydroxy-16-ethynyl-5-cis-13-trans-prostadienoic acid To a stirred, ice-cold solution of 9-oxo-11,16-dihydroxy-16-ethynyl-5-cis,1e-trans-prostadienoic acid (Example 97) in ethanol is added sodium borohydride in small portions over about one minute. The mixture is stirred at 0° for 5 minutes and at ambient temperature for about 1.5 hours. The bulk of the ethanol is evaporated at room temperature, and the residue is partitioned with cold dilute hydrochloric acid and ethyl acetate. The organic phase is separated and washed with water and brine, dried over magnesium sulfate and concentrated. The residue is chromatographed on silica gel to give an oil which is eluted first, 9,11,16-trihydroxy-16-ethynyl-5-cis,13-trans-prostadienic acid and another oil which is eluted second, 9β,11α,16-trihydroxy-16-ethynyl-5-cis,13-trans-prostadienoic acid.

EXAMPLE 166

Treatment of the 9-oxo-compounds disclosed by Examples 24 to 147 with sodium borohydride by the procedure disclosed by Example 165 followed by chromatography produced the corresponding 9α-hydroxy and 9β-hydroxy compounds (PGFα and PGFβ derivatives respectively).

EXAMPLE 167

Preparation of
11-oxo-9α,16-Dihydroxy-16-ethynyl-5-cis,13-trans-prostadienoic acid To a stirred solution of 135 mg of 9α,11α,16-trihydroxy-16-ethynyl-5-cis,13-trans-prostadienoic acid (Example 163) in acetone and acetic acid at −40° C. is added Jones Reagent. After 2 hours at −40° C. to −35° C. a few drops of isopropanol are added, and the resulting mixture is partitioned with water and ether. The ether extract is washed with water and brine, dried over magnesium sulfate, and concentrated with the oil of toluene. The residue is purified by column chromatography on silica gel with hexane progressively enriched in ethyl acetate to provide the product as an oil.

EXAMPLE 168

Oxidation of the 9α,11α,16-trihydroxy compounds derived from the selective hydride reduction of the 9-oxo compounds disclosed by Examples 24–147 produces the corresponding 9α,16-dihydroxy-11-oxo compounds (PGD derivatives).

EXAMPLE 169

In accordance with the procedure disclosed by Bundy, U.S. Pat. No. 4,060,534, incorporated by reference herein, the cycloalkyl (3 to 10 carbon atoms), aralkyl (of 7 to 12 carbon atoms), phenyl, and substituted phenyl (with from one to three chlorine atoms or alkyl of from one to three carbon atoms) esters, as disclosed therein, corresponding to the free acid compounds disclosed by Examples 24–168 may be prepared.

EXAMPLE 170

In accordance with the procedure disclosed by Morozowich, U.S. Pat. No. 3,979,440, incorporated by reference herein, the phenylacyl-type esters exemplified by the following ester groups:

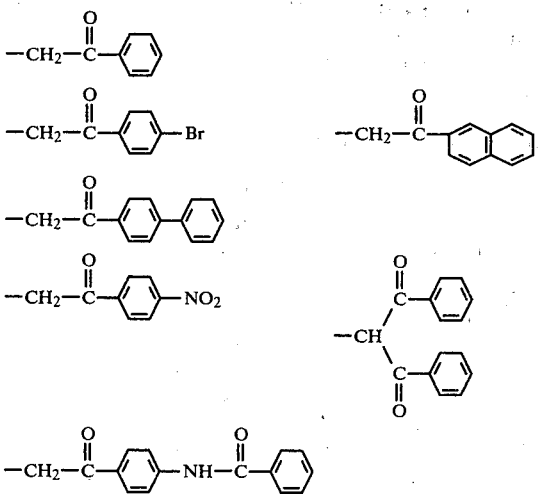

as disclosed therein, corresponding to the free acid compunds disclosed by Examples 24–168 may be prepared.

EXAMPLE 171

In accordance with the procedure disclosed by Morozowich, U.S. Pat. No. 3,929,862, incorporated by reference herein, the substituted anilide, substituted phenyl, substituted naphthyl and fluorenone esters as exemplified by the following ester groups:

a 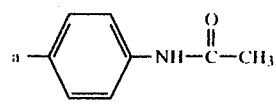
b 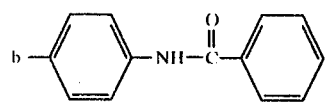
c 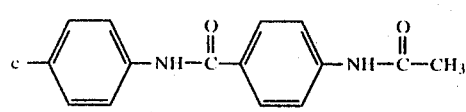
d 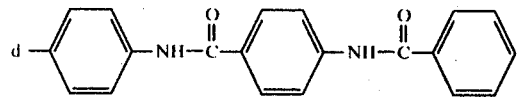
e 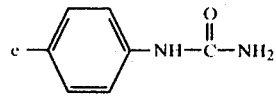
f 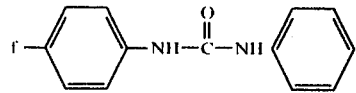
g 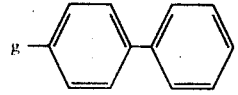
h 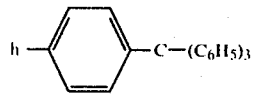
p 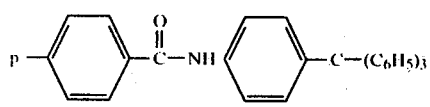
q 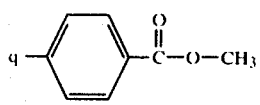
r 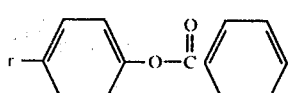
i 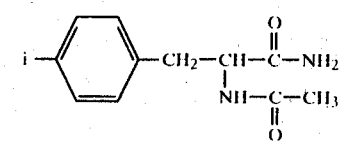
j 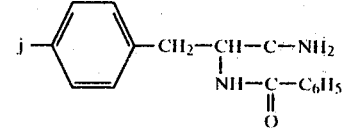
k 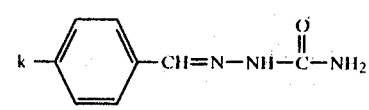
l 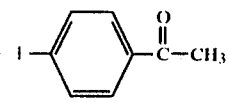
m 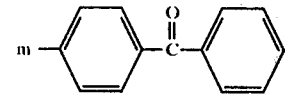
n 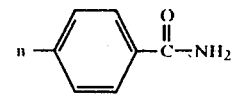
o 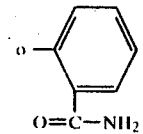
v 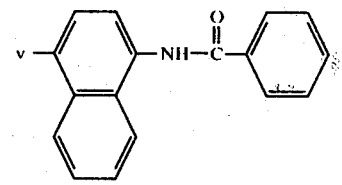
w 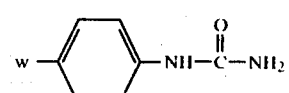
x 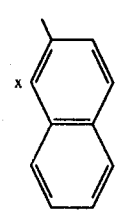
y 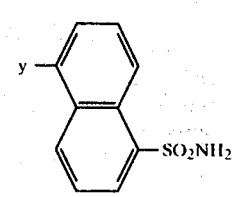

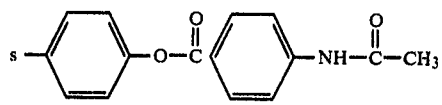
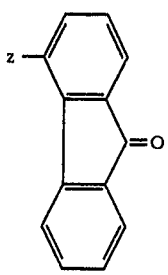
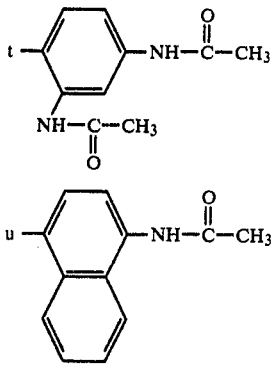

as disclosed therein, corresponding to the free acid compounds disclosed by Examples 24–168 may be prepared.

EXAMPLE 172

In accordance with the procedure disclosed by Hayashi et al., Japanese Pat. No. 74,109,341, incorporated by reference herein, the serine esters, as disclosed therein, corresponding to the free acid compounds disclosed by Examples 24–168 may be prepared.

EXAMPLE 173

In accordance with the method disclosed by Hayashi et al., U.S. Pat. No. 3,857,831, incorporated by reference herein, the carboxyalkyl esters having from 5 to 11 carbon atoms, as disclosed therein, corresponding to the free acid compounds disclosed by Examples 24 to 168 may be prepared.

EXAMPLE 174

In accordance with the procedures disclosed by Schaaf, German Off. No. 2,365,205, incorporated by reference herein, the 5-Indanyl esters, as disclosed therein, corresponding to the free acid compounds disclosed by Examples 24 to 168 may be prepared.

EXAMPLE 175

In accordance with the procedure disclosed by Hayashi et al., Japanese Pat. No. 7,425,658, incorporated by reference herein, the p-chlorophenyl, benzophenone, 2-cyclohexylethyl, and 1-phenylethyl esters corresponding to the free acid compounds disclosed by Examples 24 to 168 may be disclosed.

EXAMPLE 176

In accordance with the procedure disclosed by Belgian Pat. No. 814,520, incorporated by reference herein, the substituted benzyl, esters, as disclosed therein, corresponding to the free acid compounds disclosed by Examples 24 to 168 may be prepared.

EXAMPLE 177

In accordance with the procedure disclosed by French Pat. No. 2,240,214, incorporated by reference herein, the zeranol esters, as disclosed therein, corresponding to the free acid compounds disclosed by Examples 24–168 may be prepared.

EXAMPLE 178

In accordance with the procedure disclosed by Gordon et al., U.S. Pat. No. 3,632,627, incorporated by reference herein, the glyceride derivatives, as disclosed therein, corresponding to the free acid compounds disclosed by Examples 24 to 168 may be prepared.

EXAMPLE 179

In accordance with the procedure disclosed by Gordon et al., U.S. Pat. No. 3,746,728, incorporated by reference herein, the phosphatide derivatives, as disclosed therein, corresponding to the free acid compounds disclosed by Examples 24–168 may be prepared.

EXAMPLE 180

In accordance with the procedure disclosed by Morozowich, U.S. Pat. No. 4,005,133, incorporated by reference herein, the arginine salts, as disclosed therein, corresponding to the free acids disclosed by Examples 24 to 168 may be prepared.

EXAMPLE 181

In accordance with the procedure disclosed by Schaaf et al., U.S. Pat. No. 3,954,741, incorporated by reference herein, the N-substituted carboxamides wherein the substitution comprises alkanoyl, cycloalkanoyl, aroyl and substituted aroyl, alkylsufonyl, arylsulfonyl or substituted arylsulfonyl, as disclosed therein, corresponding to the free acid compounds disclosed by Examples 24 to 168 may be prepared.

EXAMPLE 182

In accordance with the procedure disclosed by Inukai et al., Japanese Pat. No. 7,571,650, incorporated by reference herein, the amino acid amide derivatives, as disclosed therein, corresponding to the free acid compounds disclosed by Examples 24 to 168 may be prepared.

EXAMPLE 183

In accordance with the procedure disclosed by Aries, French Pat. No. 2,258,372, incorporated by reference herein, the N-[2-hydroxy-1,1-bis(Hydroxymethyl)-ethyl]amides as disclosed therein, corresponding to the free acid compounds disclosed by Examples 24 to 168 may be prepared.

EXAMPLE 184

In accordance with the procedure disclosed by Aries, French Pat. No. 2,235,929, incorporated by reference herein, the hydrazides and substituted hydrazides, where said substitution may be alkyl, alkenyl, cycloalkyl, cycloalkenyl, aryl or aralkyl so long as the substituent has less than 11 carbon atoms, as disclosed therein, corresponding to the free acid compounds disclosed by Examples 24 to 168 may be prepared.

EXAMPLE 185

In accordance with the procedure disclosed by Japanese Pat. No. 49 069636, incorporated by reference herein, the alkyl (1 to 5 carbon atoms) amides and glycine trichloroethyl esters as disclosed therein, corresponding to the free acid compounds disclosed by Examples 24 to 168 may be prepared.

EXAMPLE 186

In accordance with the procedure disclosed by Aries, French Pat. No. 2239458, incorporated by reference herein, the amides, ethylamides and dipropylamides, as disclosed therein, corresponding to the alkyl ester compounds disclosed by Examples 24 to 168 may be prepared.

EXAMPLE 187

In accordance with the procedure disclosed by Hayashi et al., Japanese Pat. No. 7552047, incorporated by reference herein, the tryosine amides, as disclosed therein, corresponding to the free acid compounds disclosed by Examples 24 to 168 may be prepared.

EXAMPLE 188

In accordance with the procedure disclosed by Aries, French Pat. No. 2248272, incorporated by reference herein, the phthalazinylhydrazines, as disclosed therein, corresponding to the free acid compounds disclosed by Examples 24 to 168 may be prepared.

EXAMPLE 189

The compounds of this invention may be formulated with various agents which impart stability to and prolong shelf life of the resulting pharmaceutical formulation. Examples of agents which impart stability to and prolong the shelf life of the prostaglandin compounds of this invention and the corresponding reference for that formulation, which are incorporated by reference herein, are found in Table 8.

TABLE 8

| Agent | Type of Formulation | Reference |
|---|---|---|
| Thiol (such as glutatione, cysteing or acetyl-cysteine) | Freeze-dried mixture | German Offenligungschereft 2451161 |
| Water Soluble high molecular weight compound (such as dextran, dextrin, gelatin, polyvinylpyrrolidone, methylcellulose, hydroxypropylcellulose, hydroxyethylcellulose, or hydroxy carboxymethylcellulose) | | |
| Desoxycholate salt (such as an alkalimetal, arginine or lysine desoxycholate) | | |
| Calcium Lactate or Amylopectin | Freeze-dried powder | Okazaki et al., U.S. Pat. No. 4,066,787 |
| Aseptic organic solvent (such as ethyl acetate, other esters, alcohols, ketones) | Injectable Preparation | Japanese Patent No. 7343852 |
| Anhydrous, water-miscible alcohol (such as ethanol, isopropanol, 1,3-butanediol, propylene glycol, polyethylene glycol 300 or polyethylene glycol 400) | Injectable Preparation | Stehl et al., U.S. Pat. No. 3,749,800 |
| Anhydrous, water miscible, dipolar, aprotic solvent (such as N,N-dimethylacetomide, tetramethylurea, hexamethylphosphormamide, dimethylsulfoxide, sulfolane, acetone, or isopropyl methyl ketone) | Solution (for injection or steril implant) | Stehl et al., U.S. Pat. No. 3,829,579 |
| Cycloamylose | Clathrate | Japanese Patent No. 4739057 |
| Cyclodextrin | Lyophilized injectable preparations | Japanese Patent No. 49026416 |
| Cyclodextrin (such as α-β- and γ-cyclodextrins) | Clathrate | Hayashi et al., British Patent No. 1419221 |
| Cyclodextrin with ascorbic or citric acid added | Clathrate | German Patent No. 2353797 |
| Cyclodextrin (such as α, β, and γ-mixed cyclodextrin, α-cyclodextrin, β-cyclodextrin, or γ-cyclodextrin) | Clathrate | Hayashi et al., U.S. Pat. No. 3,816,393 - Hayashi et al., Patent No. 4,054,736 |
| Dialkylated mono- or polyalkylene glycol | Preparation (such as cream ointment, suppository, or solution) | German Paten No. 2358644 |
| Dialkylated mono- or polyalkylene glycol | | |

TABLE 8-continued

| Agent | Type of Formulation | Reference |
|---|---|---|
| with at least one antioxidant (for the alkylated glycol material) Diakylated polymeric mono- or polyalkylene glycol of the formula R(O—CHR$^2$—(CH$_2$)m)n—OR$^1$ where R&R$^1$ are C$_1$-C$_6$ alkyl, R$^2$ is H or C$_1$-C$_6$ alkyl, m is 1-6, and n is a number such that the compound's molecular weight is about 350 to 20,000 | | |
| Polyvinylpyrrolidone | Dry powder | O'Rourke et al., U.S. Pat. No. 3,826,823 |
| Agmatine (1-amine-4-guanidobutane, 4-(aminobutyl)-guanidine) | Complex | Zaffaroni, U.S. Pat. No. 3,845,111 |
| Putrescine (1, 4-diaminobutane, tetromethylene diamine) | | |
| Alkali metal sulfite salt (such as sodium metabisulfite, sodium sulfite, magnesium sulfite, calcium sulfite, lithium sulfite, potassium sulfite, potassium metabisulfite or potassium bisulfite) Other sulfite compounds (such as ammonium sulfite, sodium formaldehyde bisulfite, sodium formaldehyde sulfoxylate, acetone sodium bisulfite, amine complexes such as AHSO$_3$ or A$_2$SO$_3$ where A = mono,di or triethanolamine; sulfur dioxide dissolved in an aliphatic alcohol, sulfur dioxide dissolved in water to form sulfurous acid or in the presence of excess sulfur to form polythionates; or clathrates of sulfur dioxide, for example, where the cage compound is hydroquinone or phenol and the guest compound is sulfur dioxide) | Complex | Monkhouse, U.S. Pat. No. 3,851,052 |
| Amantadine (1-adamantanamine, aminoadamantane) | Salt (includes crystalline, free-flowing crystalline and non-crystalline) | Sinkula, U.S. Pat. No. 3,888,916 |
| Organic acid ester solvents (such as ethyl propionate, glycerol triacetate, ethyl n-caproate, isopropyl myristate or methyl propionate) | Solution | Hatachi et al., Japanese Patent No. 75 88,054 (5 0088-054) |
| Vegetable oils and/or esters (such as ethyl lactate) | Solution | Okazaki et al., Japanese Patent No. 75,105,815 |
| Aliphatic tertiary alcohol having from 4 to 10 carbon atoms (such as t-butanol; 2,3-dimethyl-2-butanol; 3-methyl-2-butanol; 2,3-dimethyl-3-pentanol; or 3-ethyl-3-pentanol) | Solution | Monkhouse et al., U.S. Pat. No. 3,927,197 |
| Succinic Acid Sodium Chloride Cyclodextrin Polyvinylpyrrolidone | Lypholized composition | Monkhouse et al., U.S. Pat. No. 3,954,787 |

EXAMPLE 190

Preparation of 11,16-dihydroxy-9-oxo-16-ethynyl-13-trans-prostenoic acid from the corresponding F$_{1\alpha}$ cogener To a solution of 9α,11α,16-tri-hydroxy-16-ethynyl-13-trans-prostenoic acid (Example 96) in dry acetone at −40° C. is added N-trimethylsilgdiethylamine according to the procedure of Yankee et al., *J. Chem. Soc.*, 1.121 (1972).

The reaction mixture is diluted with water and extracted with ether. The ether extract is dried and concentrated in vacuo to provide 11α-trimethylsilyloxy-9α,16-dihydroxy.

The resulting bisilylated material is oxidized with Collen's agent in situ (prepared from CrO$_3$ and pyridine in CH$_2$ Cl$_2$) according to the above reference for 5 minutes at 25° C. The material is desilylated by treatment with a mixture of methanol, water and acetic acid (1:0.1:0.05) for about an hour.

The solvent is removed in vacuo and the product is purified on silica gel to provide 11α,16-dihydroxy-9-oxo-16-ethynyl-13-trans-prostenoic acid.

EXAMPLE 191

Treatment of the PGFα compounds disclosed by Examples 24 to 188 according to the procedure disclosed by Example 190 provides the corresponding PGE compound.

EXAMPLE 192

Preparation of 11α,16-dihydroxy-9-oxo-16-ethynyl-1-acetoxy-5-cis-13-trans-prostadiene To a solution of 0.1 grams of 1,11α,16-trihydroxy-9-oxo-16-ethynyl-5-cis,13-trans-prostadiene (Example 107) in 0.75 ml pyridine is added 0.026 grams of acetic anhydride. After standing overnight, the pyridine is removed at reduced pressure. The residue is chromatographed on a dry column of silica gel eluting with benzene-ethyl acetate 1:1 to give the product compound.

EXAMPLE 193

In accordance with the procedure disclosed by Example 192, the 1-carbinol compounds disclosed by Examples 24 to 188 may be treated with acetic anhydride, propionic anhydride, n-butyric anhydride and n-valeric anhydride to give the corresponding 1-acetoxy, 1-propanoyloxy, 1-n-butanoyloxy, and 1-n-pentanoyloxy compounds.

EXAMPLE 194

Preparation of
11α,16-dihydroxy-9-oxo-1-p-methoxybenzoxy-16-ethynyl-13-trans-prostene To a mixture of 200 mg of 1,11α,16-trihydroxy-9-oxo-16-ethynyl-13-trans-prostene (Example 106) and 89.2 mg (1 eq) of p-anisoylchloride is added 2 ml of dry pyridine. After agitation to complete dissolution, the solution is allowed to stand at ambient temperature for about 2 hours. The solution is applied directly to a silica-gel dry column (31"×1") and developed with ethyl acetate. The column is segmented and the fractions containing the product ester are eluted with ethyl acetate to yield the product compound.

EXAMPLE 195

Preparation of
11α,16-dihydroxy-9-oxo-1-p-chlorobenzoxy-16-ethynyl-13-trans-prostene To a mixture of 303 mg of 1,11α,16-trihydroxy-9-oxo-16-ethynyl-13-trans-prostene (Example 106) and 139 mg (1 eq) of p-chlorobenzoylchloride is added 2.5 ml of dry pyridine. After dissolution, the reaction mixture is allowed to stand about 18 hours at ambient temperature. The reaction mixture is placed directly onto a silica-gel dry column (50"×1") containing 225 grams of silica gel and developed with ethyl acetate. The column is segmented and the sections containing the product are eluted with ethyl acetate to provide the product ester as a wax.

EXAMPLE 196

Preparation of
11α,16-dihydroxy-9-oxo-1-carbethoxyoxy-16-ethynyl-13-trans-prostene To a mixture of 200 mg of 1,11α,16-trihydroxy-9-oxo-16-ethynyl-13-trans-prostene (Example 106) and 57 mg (1 eq) of ethyl chloroformate is added 1.5 ml of dry pyridine. After stirring at ambient temperature for 18 hours the mixture is applied directly to a 31"×1" dry column of silica gel and developed with ethyl acetate. The column is segmented and the portion containing the product is washed with ethyl acetate to give the product carbonate.

EXAMPLE 197

Preparation of
11α,16-dihydroxy-9-oxo-1-acetoxy-16-ethynyl-13-trans-prostene

To a solution of 218 mg of 1,11α,16-trihydroxy-9-oxo-16-ethynyl-13-trans-prostene (Example 106) in 1 ml of dry pyridine at 0° C. is added, dropwise, a solution of 58 mg (1 eq) of acetic anhydride in 0.6 ml of dry pyridine. After stirring at 0° C. for 18 hours, the reaction mixture is placed directly onto a silica-gel dry column (150 grams silica-gel, 35"×1", equilibrated with 15 ml ETOAC) and developed with ethyl acetate. The column is segmented and the portions containing the product are eluted with ethyl acetate to give the 1-acetoxy product.

EXAMPLE 198

In accordance with the procedure disclosed by Example 194, the 1-methoxybenzoxy compounds corresponding to the 1-carbinol compounds disclosed by Examples 24–182 may be prepared.

EXAMPLE 199

In accordance with the procedure disclosed by Example 195, the 1-p-chlorobenzoxy compounds corresponding to the 1-carbinol compounds disclosed by Examples 24 to 188 may be prepared.

EXAMPLE 200

In accordance with the procedure disclosed by Example 196, the 1-carbethoxyoxy compounds corresponding to the 1-carbinol compounds disclosed by Examples 24 to 188 may be prepared.

EXAMPLE 201

In accordance with procedure disclosed by Example 197, the 1-acetoxy compounds corresponding to the 1-carbinol compounds disclosed by Examples 24 to 188 may be prepared.

EXAMPLE 202

Treatment of 1,11α,16-trihydroxy-9-oxo-16-ethynyl-13-trans-prostene (Example 106) or the individual optical isomers thereof with about 1.1 eq of the following acid halides by the procedure of Examples 194 to 196 or a carboxylic acid anhydride by the procedure of Example 197 provides the corresponding 1-substituted carboxy prostanoic derivative.

CARBOXYLIC HALIDES

Acetyl Bromide
Acetyl Chloride
O-Acetylmandelic acid chloride
O-Acetylisalicyloyl chloride
Acryloyl chloride
1-Adamantanecarboxylic acid chloride
p-Anisoyl chloride
Benzoyl bromide
Benzoyl chloride
4-Biphenylcarbonyl chloride
Bromoacetyl chloride
2-Bromobenzoyl chloride
4-Bromobenzoyl chloride
2-Bromo-2,2-diphenylacetyl bromide
2-Bromoproppionyl chloride
3-Bromopropionyl chloride
p-tert,Butylacetyl chloride
tert-Butylacetyl chloride
Butyryl chloride
3-Carbomethoxypropionyl chloride
Chloroacetyl chloride
o-Chlorobenzoyl chloride
m-Chlorobenzoyl chloride
p-Chlorobenzoyl chloride
4-Chlorobutyryl chloride
α-Chloro-α,α-diphenylacetyl chloride
p-(Chloroformyl)-phenyl methyl carbonate
α-Chlorophenylacetyl chloride
2-Chloropropionyl chloride 3-Chloropropionyl chloride
5-Chlorovaleryl chloride
Cinnamoyl chloride
Crotonyl chloride
4-Cyanobenzoyl chloride
Cyclobutanecarboxylic acid chloride
Cyclohexanecarboxylic acid chloride
Cyclopropanecarboxylic acid chloride
Decanoyl chloride
Dichloroacetyl chloride
2,4-Dichlorobenzoyl chloride
2,6-Dichlorobenzoyl chloride
3,4-Dichlorobenzoyl chloride
Diethylcarbamyl chloride
3,5-Dimethoxybenzoyl chloride
3,3-Dimethylacryloyl chloride
3,5-Dinitrobenzoyl chloride
Diphenylcarbamyl chloride
trans-3,6-Endomethylene-1,2,3,6-tetrahydrophthaloyl chloride
2-Ethylhexanoyl chloride
Ethyl malonyl chloride
Ethyl oxalyl chloride
Ethyl succinyl chloride
o-Fluorobenzoyl chloride
m-Fluorobenzoyl chloride
p-Fluorobenzoyl chloride
2-Furoyl chloride
Hexanoyl chloride
Isobutyryl chloride
Isophthaloyl dichloride
Isovaleryl chloride
Itaconyl chloride
Lauroyl chloride
Methacryloyl chloride
Methoxyacetyl chloride
Methyl 4-(chloroformyl)-butyrate
Methyl oxalyl chloride
Myristoyl chloride
m-Nitrobenzoyl chloride
p-Nitrobenzoyl chloride
Nonanoyl chloride
5-Norbornene-2-carbonyl chloride
Octanoyl chloride
Palmitoyl chloride
Pentafluorobenzoyl chloride
Phenoxyacetyl chloride
Phenylacetyl chloride
trans-2-Phenylcyclopropane-1-carboxylic acid chloride
Propionyl chloride
2-Quinoxaloyl chloride
Terephthaloyl chloride
o-Toluoyl chloride
n-Toluoyl chloride
p-Toluoyl chloride
3,4,5-Trimethoxybenzoyl chloride
Trimethylacetyl chloride
10-Undecenoyl chloride
Valeryl chloride

CARBOXYLIC ACID ANHYDRIDES

Acetic anhydride
n-Butyric anhydride
2,2-dimethylglutaric anhydride
3,3-dimethylglutaric anhydride
2,3-dimethyl glutaric anhydride
Heptafluorobutyric anhydride
Homophthalic anhydride
Maleic anhydride
3-methylglutaric anhydride
Methylsuccinic anhydride
Propionic anhydride
Succinic anhydride
3,3-tetramethylene glutaric anhydride
benzoic anhydride
Phthalic anhydride
3-nitrophthalic anhydride
Tetrabromophthalic anhydride
Tetrachlorophthalic anhydride
dl-Camphoric anhydride
cis-1,2-Cyclobutanedicarboxylic anhydride
cis-1,2-Cyclohexanedicarboxylic anhydride
Hexahydro-4-methylphthalic anhydride
cis-1,2,3,6-Tetrahydrophthalic anhydride
3,4,5,6-Tetrahydrophthalic anhydride

EXAMPLE 203

Treatment of the 1-carbinol compounds disclosed by Examples 24–188, or the individual isomers thereof, with about 1.1 eq of the acid halides or anhydrides listed in Example 202 by the procedures of Examples 194 to 197 is productive of the corresponding 1-substituted carboxy compound.

A 15-deoxy-16-hydroxy substituted prostaglandin consists of two dl racemates ie. 16α-hydroxyl and 16β-hydroxyl which are separable into the 16α- and 16β-epimers. A species claim wherein the stereochemistry of the $C_{16}$ carbon is not specified encompasses the nat. 16α- and nat. 16β- forms of the compound and the racemic mixtures thereof.

This invention has been described in terms of specific embodiments set forth in detail herein, but, it should be understood that these are by way of illustration only and that the invention is not necessarily limited thereto. Modifications and variations will be apparent from this disclosure and may be resorted to without departing from the spirit of this invention, as those skilled in the art will understand. Accordingly, such variations and modifications of the disclosed invention are considered to be within the purview and scope of this invention and the following claims.

We claim:

1. An optically active compound of the formula

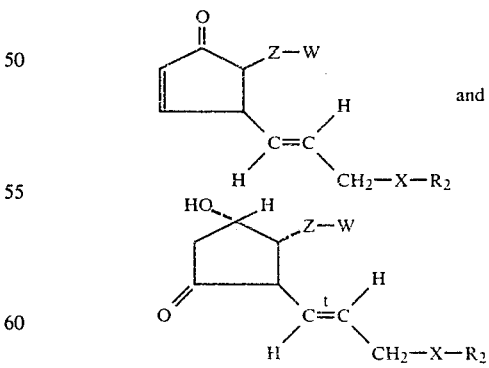

wherein W is;

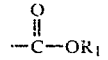

$R_1$ is selected from the group consisting of hydrogen and $C_1$ to $C_6$ alkyl; $R_2$ is selected from the group consisting of $C_3$ to $C_7$ alkyl; X is selected from the group consisting of a divalent moiety of the formula

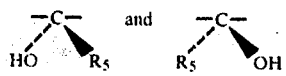

$R_5$ is selected from the group consisting of 1-propynyl, ethynyl and trimethylsilylethynyl; Z is selected from the group $-(CH_2)_6-$,

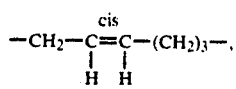

$-(CH_2)_4-S-CH_2-$ and $-(CH_2)_4-O-CH_2-$; with the proviso that when Z is selected from the group $-(CH_2)_6-$, $-(CH_2)_4-S-CH_2-$ and $-(CH_2)_4-O-CH_2-$ then the compounds cannot be

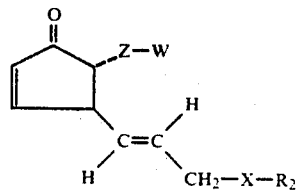

the racemic mixtures thereof, and when $R_1$ is hydrogen, the pharmacologically acceptable salts thereof.

2. The optically active and racemic compounds of claim 1 having the formula

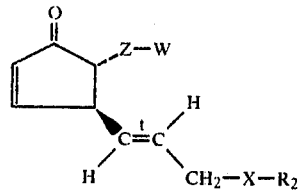

wherein Z, W, X and $R_2$ are as previously defined.

3. A compound according to claim 2 wherein Z is

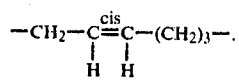

4. The compound according to claim 3 ethyl-16-hydroxy-9-oxo-16-ethynyl-5-cis,10,13-trans-prostatrienoate.

5. The compound according to claim 3 ethyl-16-hydroxy-9-oxo-16-ethynyl-20-ethyl-5-cis,10,13-trans-prostatrienoate.

6. The optically active and racemic compounds of claim 1 having the formula

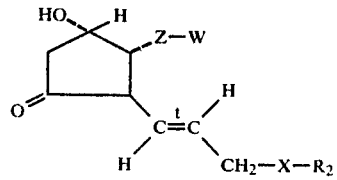

7. A compound according to claim 6 wherein Z is $-(CH_2)_6-$.

8. A compound according to claim 6 wherein Z is

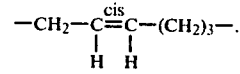

* * * * *